US007355028B2

(12) United States Patent
Zelder et al.

(10) Patent No.: US 7,355,028 B2
(45) Date of Patent: Apr. 8, 2008

(54) GENES ENCODING GENETIC STABILITY, GENE EXPRESSION AND FOLDING PROTEINS

(75) Inventors: Oskar Zelder, Speyer (DE); Markus Pompejus, Freinsheim (DE); Hartwig Schröder, Nußloch (DE); Burkhard Kröger, Limburgerhof (DE); Corinna Klopprogge, Mannheim (DE); Gregor Haberhauer, Limburgerhof (DE)

(73) Assignee: BASF AG, Ludwigshafen (DE)

( * ) Notice: Subject to any disclaimer, the term of this patent is extended or adjusted under 35 U.S.C. 154(b) by 0 days.

(21) Appl. No.: 11/592,903

(22) Filed: Nov. 3, 2006

(65) Prior Publication Data

US 2007/0054381 A1 Mar. 8, 2007

Related U.S. Application Data

(62) Division of application No. 10/494,541, filed as application No. PCT/EP02/12138 on Oct. 31, 2002, now Pat. No. 7,138,513.

(30) Foreign Application Priority Data

Nov. 5, 2001 (DE) ................................ 101 54 180

(51) Int. Cl.

| | |
|---|---|
| ***C07H 21/04*** | (2006.01) |
| ***C12N 1/20*** | (2006.01) |
| ***C12N 15/00*** | (2006.01) |
| ***C12P 21/06*** | (2006.01) |

(52) U.S. Cl. ................. 536/23.7; 435/69.1; 435/252.1; 435/320.1

(58) Field of Classification Search .............. 536/23.7; 435/69.1, 252.1, 320.1
See application file for complete search history.

(56) References Cited

U.S. PATENT DOCUMENTS

2002/0197605 A1 12/2002 Nakagawa et al.

FOREIGN PATENT DOCUMENTS

| | | | |
|---|---|---|---|
| DE | 19929365 | A1 | 12/2000 |
| EP | 1108790 | A2 | 6/2001 |
| WO | WO-01/00804 | A2 | 1/2001 |
| WO | WO-01/04322 | A1 | 1/2001 |

OTHER PUBLICATIONS

Bathe, Brigitte et al., "A physical and genetic map of the *Corynebacterium glutamicum* ATCC 13032 chromosome," *Mol. Gen. Genet.*, vol. 252:255-265 (1996).

GenBank Accession No. AP005279, Nakagawa, S., "Complete genomic sequence of *Corynebacterium glutamicum* ATCC 13032," (2002).

European Search Report for Application No. 06110205.9—2401, dated Nov. 23, 2006.

*Primary Examiner*—Mark Navarro
(74) *Attorney, Agent, or Firm*—Lahive & Cockfield, LLP; Elizabeth A. Hanley; Maria Laccotripe Zacharakis

(57) ABSTRACT

The invention relates to novel nucleic acid molecules, to the use thereof for constructing genetically improved microorganisms and to methods for preparing fine chemicals, in particular amino acids, with the aid of said genetically improved microorganisms.

19 Claims, No Drawings

GENES ENCODING GENETIC STABILITY, GENE EXPRESSION AND FOLDING PROTEINS

RELATED APPLICATIONS

The present application is a divisional of U.S. application Ser. No. 10/494,541, filed May 3, 2004 now U.S. Pat. No. 7,138,513 which is a 35 U.S.C. 371 national stage filing of International Application No. PCT/EP02/12138, filed Oct. 31, 2002, which claims priority to German Application No. 101 54 180.5, filed Nov. 5, 2001. The entire contents of each of these applications are hereby incorporated by reference herein.

INCORPORATION OF MATERIAL SUBMITTED ON COMPACT DISCS

This application incorporates herein by reference the material contained on the compact discs submitted herewith as part of this application. Specifically, the file "Seqlist" (545 KB) contained on each of Copy 1 and Copy 2 of the Sequence Listing is hereby incorporated herein by reference. This file was created on Oct. 31, 2006.

BACKGROUND OF THE INVENTION

Particular products and byproducts of naturally occurring metabolic processes in cells are used in many branches of industry, including the food industry, the animal feed industry, the cosmetics industry and the pharmaceutical industry. These molecules which are collectively referred to as "fine chemicals" comprise organic acids, both proteinogenic and nonproteinogenic amino acids, nucleotides and nucleosides, lipids and fatty acids, diols, carbohydrates, aromatic compounds, vitamins, cofactors and enzymes. They are best produced by means of cultivating, on a large scale, bacteria which have been developed to produce and secrete large amounts of the molecule desired in each particular case. An organism which is particularly suitable for this purpose is *Corynebacterium glutamicum,* a Gram-positive nonpathogenic bacterium. Using strain selection, a number of mutant strains have been developed which produce various desirable compounds. The selection of strains which are improved with respect to the production of a particular molecule is, however, a time-consuming and difficult process.

BRIEF DESCRIPTION OF THE INVENTION

The present invention provides novel nucleic acid molecules which can be used for identifying or classifying *Corynebacterium glutamicum* or related bacterial species. *C. glutamicum* is a Gram-positive, aerobic bacterium which is normally widely used in industry for the large-scale production of a number of fine chemicals and also for the degradation of hydrocarbons (for example in the case of crude oil spills) and for the oxidation of terpenoids. The nucleic acid molecules may therefore be used for identifying microorganisms which can be used for producing fine chemicals, for example by fermentation processes. Although *C. glutamicum* itself is nonpathogenic, it is, however, related to other *Corynebacterium* species such as *Corynebacterium diphteriae* (the diphtheria pathogen), which are major pathogens in humans. The ability to identify the presence of *Corynebacterium* species may therefore also be of significant clinical importance, for example in diagnostic applications. Moreover, said nucleic acid molecules may serve as reference points for mapping the *C. glutamicum* genome or genomes of related organisms.

These novel nucleic acid molecules encode proteins which are referred to herein as proteins for gene stability, gene expression or protein secretion/protein folding (SES proteins). These SES proteins may, for example, exert a function which is involved in repair or recombination of DNA, transposition of genetic material, expression of genes (i.e. which are involved in transcription or translation), protein folding or protein secretion in *C. glutamicum.* Owing to the availability of cloning vectors which can be used in *Corynebacterium glutamicum,* as disclosed, for example in Sinskey et al., U.S. Pat. No. 4,649,119, and of techniques for the genetic manipulation of *C. glutamicum* and the related *Brevibacterium* species (e.g. *lactofermentum*) (Yoshihama et al., J. Bacteriol. 162: 591-597 (1985); Katsumata et al., J. Bacteriol. 159: 306-311 (1984); and Santamaria et al. J. Gen. Microbiol. 130: 2237-2246 (1984)), the nucleic acid molecules of the invention can be used for genetic manipulation of said organism in order to make it a more efficient producer of one or more fine chemicals. This improved production or efficiency of production of a fine chemical may be caused directly by manipulation of a gene of the invention or indirectly by such a manipulation.

There is a number of mechanisms by which modification of an SES protein of the invention can directly influence the yield, production and/or efficiency of production of a fine chemical from a *C. glutamicum* strain containing this modified protein. For example, modulation of proteins directly involved in transcription or translation (e.g. polymerases or ribosomes) so as to increase their number or activity should overall increase cellular transcription or translation (or the rate of these processes). This increased cellular gene expression should include those proteins which are involved in the biosynthesis of fine chemicals so that the yield, production or efficiency of production of one or more compounds of interest can be increased. Modifications of the transcriptional/translational protein machinery of *C. glutamicum* so as to modify regulation of these proteins may also enable the increased expression of genes involved in the production of fine chemicals. Modulation of the activity of a number of proteins involved in peptide folding may increase the overall production of correctly folded molecules in the cell, thereby increasing the possibility of proteins of interest (e.g. proteins of the biosynthesis of fine chemicals) functioning correctly. Furthermore, it may be possible, by mutating proteins involved in the secretion from *C. glutamicum* so as to increase their number or activity, to increase secretion of a fine chemical (e.g. an enzyme) from cells in a fermentative culture from which said fine chemical can be readily obtained.

Genetic modification of the SES molecules of the invention may also modulate indirectly the production of one or more fine chemicals. For example, it is possible, by increasing the number or activity of a DNA-repair or DNA-recombination protein of the invention, to increase the ability of the cell to detect and repair DNA damage. This should effectively increase the ability of the cell to keep a mutated gene in its genome and thereby increase the probability of a transgene genetically introduced into *C. glutamicum* (which encodes, for example, a protein which increases the biosynthesis of a fine chemical) not being lost during cultivation of the microorganism. In contrast, it may be possible, by reducing the number or activity of one or more DNA-repair or DNA-recombination proteins, to increase the genetic instability of the organism. These manipulations should improve the ability of said organism to be modified by mutagenesis, without correcting the introduced mutation. The same is true for proteins which are involved in the transposition or rearrangement of genetic elements in *C. glutamicum* (e.g. transposons). Mutagenesis of these proteins so as to either increase or reduce their number or activity makes it possible to increase or reduce at the same time the genetic stability of the microorganism. This crucially affects the possibility of introducing another mutation into *C. glutamicum* and of retaining the introduced mutation. Transposons likewise provide a suitable mechanism which makes possible the mutagenesis of *C. glutamicum;* duplication of genes of interest (e.g. genes of the biosynthesis of fine chemicals) as well as disruption of unwanted genes (e.g. genes involved in the degradation of fine chemicals of interest) can be readily carried out by means of transposon mutagenesis.

It may be possible, by modulating one or more proteins (e.g. sigma factors) which are involved in the regulation of transcription or translation in reaction to particular environmental conditions, to prevent the cell from slowing down or stopping protein synthesis under unfavorable environmental conditions as found in a large-scale fermentative culture. This should increase gene expression, and this in turn may enable the increased biosynthesis of fine chemicals of interest under said conditions. Mutagenesis of proteins involved in secretion systems may result in modulated secretion rates. Many of these secreted proteins have functions which are important for cell viability (e.g. cell surface proteases or cell surface receptors). A change in the secretion pathway so that these proteins are transported more readily to their extracellular location may increase the overall viability of the cell and thus result in higher numbers of *C. glutamicum* cells able to produce fine chemicals during large-scale cultivation. It is furthermore known that the secretion apparatus (e.g. the sec system) is also involved in the insertion of integral membrane proteins (e.g. pores, channels or transporters) into the membrane. Thus, modulation of the activity of proteins involved in protein secretion from *C. glutamicum* may influence the ability of the cell to secrete waste products or to import necessary metabolites. If the activity of these secretory proteins is increased, the ability of the cell to produce fine chemicals may likewise be increased. If the activity of said secretory proteins is reduced, there may not be enough nutrients to support overproduction of compounds of interest or waste products may interfere with this biosynthesis.

The invention provides novel nucleic acid molecules encoding proteins which are referred to herein as SES proteins and which may be involved, for example, in the repair or recombination of DNA, transposition of genetic material, expression of genes (i.e. in transcriptional or translational processes), protein folding or protein secretion in *Corynebacterium glutamicum*. Nucleic acid molecules encoding an SES protein are referred to herein as SES nucleic acid molecules. In a preferred embodiment, an SES protein is involved in improving or reducing the genetic stability in *C. glutamicum,* in the expression of genes (e.g. in transcription or translation) or in protein folding in this organism or in protein secretion from *C. glutamicum.* Examples of such proteins are those encoded by the genes listed in Table 1.

Consequently, one aspect of the invention relates to isolated nucleic acid molecules (e.g. cDNAs) comprising a nucleotide sequence which encodes an SES protein or biologically active sections thereof and also nucleic acid fragments which are suitable as primers or hybridization probes for detecting or amplifying SES-encoding nucleic acid (e.g. DNA or mRNA). In particularly preferred embodiments, the isolated nucleic acid molecule comprises any of the nucleotide sequences listed in Appendix A or the coding region or a complement thereof of any of these nucleotide sequences. In other preferred embodiments, the isolated nucleic acid molecule encodes any of the amino acid sequences listed in Appendix B. The preferred SES proteins of the invention likewise have preferably at least one of the SES activities described herein.

Appendix A defines hereinbelow the nucleic acid sequences of the sequence listing together with the sequence modifications at the relevant position, described in Table 1.

Appendix B defines hereinbelow the polypeptide sequences of the sequence listing together with the sequence modifications at the relevant position, described in Table 1.

In a further embodiment, the isolated nucleic acid molecule is at least 15 nucleotides in length and hybridizes under stringent conditions to a nucleic acid molecule which comprises a nucleotide sequence of Appendix A. Such stringent conditions, for example, hybridization in 6×sodium chloride/sodium citrate (SSC) at about 45° C., followed by one or more washes in 0.2×SSC, 0.1% SDS at 50-65° C., are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning: A Laboratory Manual*, Sambrook et al., Cold Spring Harbor Press, Cold Spring Harbor, N.Y. (1989), chapters 7, 9, and 11. The isolated nucleic acid molecule preferably corresponds to a naturally occuffing nucleic acid molecule. The isolated nucleic acid more preferably encodes a naturally occurring *C. glutamicum* SES protein or a biologically active section thereof.

A further aspect of the invention relates to vectors, for example recombinant expression vectors, which contain the nucleic acid molecules of the invention and to host cells into which said vectors have been introduced. In one embodiment, an SES protein is prepared by using said host cell which is cultivated in a suitable medium. The SES protein may then be isolated from the medium or the host cell.

A further aspect of the invention relates to a genetically modified microorganism into which an SES gene has been introduced or in which an HA gene has been modified. In one embodiment, the genome of said microorganism has been modified by introducing at least one inventive nucleic acid molecule which encodes the mutated SES sequence as transgene. In another embodiment, an endogenous SES gene in the genome of said microorganism has been modified, for example, functionally disrupted, by homologous recombination with a modified SES gene. In a preferred embodiment, the microorganism belongs to the genus *Corynebacterium* or *Brevibacterium,* with *Corynebacterium glutamicum* being particularly preferred. In a preferred embodiment, the microorganism is also used for preparing a compound of interest, such as an amino acid,lysine being particularly preferred.

A further aspect of the invention relates to an isolated SES protein or a section therof, for example a biologically active section. In a preferred embodiment, the isolated SES protein or its section may take part in the repair or recombination of DNA, transposition of genetic material, gene expression (i.e. transcriptional or translational processes), protein folding or protein secretion in *Corynebacterium glutamicum.* In another preferred embodiment, the isolated SES protein or a section thereof is sufficiently homologous to an amino acid sequence of Appendix B for the protein or its section to retain the ability, for example, to take part in the repair or recombination of DNA, transposition of genetic material, gene expression (i.e. transcriptional or translational processes), protein folding or protein secretion in *Corynebacterium glutamicum*.

Another preferred embodiment are host cells having more than one of the nucleic acid molecules described in Appendix A. Such host cells can be prepared in various ways known to the skilled worker. They may be transfected, for example, by vectors carrying several of the nucleic acid molecules of the invention. However, it is also possible to use a vector for introducing in each case one nucleic acid molecule of the invention into the host cell and therefore to use a plurality of vectors either simultaneously or sequentially. Thus it is possible to construct host cells which carry numerous, up to several hundred, nucleic acid sequences of the invention. Such an accumulation can often produce superadditive effects on the host cell with respect to fine-chemical productivity.

Moreover, the invention provides an isolated SES protein preparation. In preferred embodiments, the SES protein comprises an amino acid sequence of Appendix B. In a further preferred embodiment, the invention relates to an isolated full-length protein which is essentially homologous to a complete amino acid sequence of Appendix B (which is encoded by an open reading frame in Appendix A).

The SES polypeptide or a biologically active section thereof may be functionally linked to a non-SES polypeptide in order to produce a fusion protein. In preferred embodiments, this fusion protein has a different activity from that of the SES protein alone. In other preferred embodiments, said fusion protein takes part in the repair or recombination of DNA, transposition of genetic material, gene expression (i.e. transcriptional or translational processes), protein folding or protein secretion in *Corynebacterium glutamicum*. In particularly preferred embodiments, integration of said fusion protein into a host cell modulates the production of a compound of interest by the cell.

A further aspect of the invention relates to a method for preparing a fine chemical. The method provides for the cultivation of a cell containing a vector which causes expression of an SES nucleic acid molecule of the invention so that a fine chemical is produced. In a preferred embodiment, this method moreover comprises the step of obtaining a cell containing such a vector, said cell being transfected with a vector which causes expression of an SES nucleic acid. In a further preferred embodiment, said method moreover comprises the step in which the fine chemical is obtained from the culture. In a particularly preferred embodiment, the cell belongs to the genus *Corynebacterium* or *Brevibacterium*.

A further aspect of the invention relates to methods for modulating the production of a molecule from a microorganism. These methods comprise contacting the cell with a substance which modulates SES-protein activity or SES nucleic-acid expression such that a cell-associated activity is modified in comparison with the same activity in the absence of said substance. In a preferred embodiment, the cell is modulated with regard to one or more *C. glutamicum* processes which are involved in genetic stability, gene expression, protein folding or protein secretion, so as to improve the yield, production or efficiency of production of a fine chemical of interest by this microorganism. The substance which modulates SES protein activity may be a substance which stimulates SES-protein activity or SES nucleic-acid expression. Examples of substances stimulating SES protein activity or SES nucleic-acid expression include small molecules, active SES proteins and nucleic acids which encode SES proteins and have been introduced into the cell. Examples of substances which inhibit SES activity or SES expression include small molecules and SES antisense nucleic acid molecules.

A further aspect of the invention relates to methods for modulating the yields of a compound of interest from a cell, comprising introducing an SES wild-type gene or HA-mutant gene into a cell, which gene either remains on a separate plasmid or is integrated into the genome of the host cell. Integration into the genome may take place randomly or via homologous recombination so that the native gene is replaced by the introduced copy, leading to the production of the compound of interest from the cell to be modulated. In a preferred embodiment, said yields are increased. In a further preferred embodiment, the chemical is a fine chemical which, in a particularly preferred embodiment, is an amino acid. In a particularly preferred embodiment, this amino acid is L-lysine.

DETAILED DESCRIPTION OF THE INVENTION

The present invention provides SES nucleic acid and SES-protein molecules which are involved in the repair or recombination of DNA, transposition of genetic material, gene expression (i.e. transcriptional or translational processes), protein folding or protein secretion in *Corynebacterium glutamicum*. The molecules of the invention can be used for modulating the production of fine chemicals from microorganisms such as *C. glutamicum* either directly (for example, if overexpression or optimization of the activity of a protein involved in the secretion of a fine chemical (e.g. an enzyme) has a direct effect on the yield, production and/or efficiency of production of a fine chemical from the modified *C. glutamicum* cells) or via an indirect effect which nevertheless causes an increase in the yield, production and/or efficiency of the compound of interest (for example, if modulating the activity or copy number of a *C. glutamicum* DNA-repair protein to changes in the ability of the microorganism to maintain the introduced mutation, and this in turn may influence the production of one or more fine chemicals from said strain). The aspects of the invention are further illustrated below.

I. Fine Chemicals

The term "fine chemicals" is known in the art and includes molecules which are produced by an organism and are used in various branches of industry such as, for example, but not restricted to, the pharmaceutical industry, the agricultural industry and the cosmetics industry. These compounds comprise organic acids such as tartaric acid, itaconic acid and diaminopimelic acid, both proteinogenic and nonproteinogenic amino acids, purine and pyrimidine bases, nucleosides and nucleotides (as described, for example, in Kuninaka, A. (1996) Nucleotides and related compounds, pp. 561-612, in Biotechnology Vol. 6, Rehm et al., Editors VCH: Weinheim and the references therein), lipids, saturated and unsaturated fatty acids (e.g. arachidonic acid), diols (e.g. propanediol and butanediol), carbohydrates (e.g. hyaluronic acid and trehalose), aromatic compounds (e.g. aromatic amines, vanilline and indigo), vitamins and cofactors (as described in Ullmann's Encyclopedia of Industrial Chemistry, Vol. A27, "Vitamins", pp. 443-613 (1996) VCH: Weinheim and the references therein; and Ong, A. S., Niki, E. and Packer, L. (1995) "Nutrition, Lipids, Health and Disease" Proceedings of the UNESCO/Confederation of Scientific and Technological Associations in Malaysia and the Society for Free Radical Research—Asia, held Sep. 1-3, 1994 in Penang, Malaysia, AOCS Press (1995)), enzymes and all other chemicals described by Gutcho (1983) in Chemicals by Fermentation, Noyes Data Corporation, ISBN: 0818805086 and the references indicated therein. The metabolism and the uses of particular fine chemicals are further illustrated below.

A. Metabolism and Uses of Amino Acids

Amino acids comprise the fundamental structural units of all proteins and are thus essential for normal functions of the cell in all organisms. The term "amino acid" is known in the art. Proteinogenic amino acids, of which there are 20 types, serve as structural units for proteins, in which they are linked together by peptide bonds, whereas the nonproteinogenic amino acids (hundreds of which are known) usually do not occur in proteins (see Ullmann's Encyclopedia of Industrial Chemistry, Vol. A2, pp. 57-97 VCH: Weinheim (1985)). Amino acids can exist in the optical D or L configuration, although L-amino acids are usually the only type found in naturally occurring proteins. Biosynthetic and degradation pathways of each of the 20 proteinogenic amino acids are well characterized both in prokaryotic and eukaryotic cells (see, for example, Stryer, L. Biochemistry, 3rd edition, pp. 578-590 (1988)). The "essential" amino acids (histidine, isoleucine, leucine, lysine, methionine, phenylalanine, threonine, tryptophan and valine), so called because, owing to the complexity of their biosyntheses, they must usually be taken in with the diet, are converted by simple biosynthetic pathways into the other 11 "nonessential" amino acids (alanine, arginine, asparagine, aspartate, cysteine, glutamate, glutamine, glycine, proline, serine and tyrosine). Higher animals are able to synthesize some of these amino acids but the essential amino acids must be taken in with the food in order that normal protein synthesis takes place.

Apart from their function in protein biosynthesis, these amino acids are interesting chemicals as such, and it has been found that many have various applications in the human food, animal feed, chemicals, cosmetics, agricultural and pharmaceutical industries. Lysine is an important amino acid not only for human nutrition but also for monogastric livestock such as poultry and pigs. Glutamate is most frequently used as flavor additive (monosodium glutamate, MSG) and elsewhere in the food industry, as are aspartate, phenylalanine, glycine and cysteine. Glycine, L-methionine and tryptophan are all used in the pharmaceutical industry. Glutamine, valine, leucine, isoleucine, histidine, arginine, proline, serine and alanine are used in the pharmaceutical industry and the cosmetics industry. Threonine, tryptophan and D/L-methionine are widely used animal feed additives (Leuchtenberger, W. (1996) Amino acids—technical production and use, pp. 466-502 in Rehm et al., (editors) Biotechnology Vol. 6, Chapter 14a, VCH: Weinheim). It has been found that these amino acids are additionally suitable as precursors for synthesizing synthetic amino acids and proteins, such as N-acetylcysteine, S-carboxymethyl-L-cysteine, (S)-5-hydroxytryptophan and other substances described in Ullmann's Encyclopedia of Industrial Chemistry, Vol. A2, pp. 57-97, VCH,. Weinheim, 1985.

The biosynthesis of these natural amino acids in organisms able to produce them, for example bacteria, has been well characterized (for a review of bacterial amino acid biosynthesis and its regulation, see Umbarger, H. E. (1978) Ann. Rev. Biochem. 47: 533-606). Glutamate is synthesized by reductive amination of α-ketoglutarate, an intermediate product in the citric acid cycle. Glutamine, proline and arginine are each generated successively from glutamate. The biosynthesis of serine takes place in a three-step process, starts with 3-phosphoglycerate (an intermediate product of glycolysis), and affords this amino acid after oxidation, transamination and hydrolysis steps. Cysteine and glycine are each produced from serine, specifically the former by condensation of homocysteine with serine, and the latter by transfer of the side-chain β-carbon atom to tetrahydrofolate in a reaction catalyzed by serine transhydroxy-methylase. Phenylalanine and tyrosine are synthesized from the precursors of the glycolysis and pentose phosphate pathway, and erythrose 4-phosphate and phosphoenolpyruvate in a 9-step biosynthetic pathway which diverges only in the last two steps after the synthesis of prephenate. Tryptophan is likewise produced from these two starting molecules but it is synthesized by an 11-step pathway. Tyrosine can also be prepared from phenylalanine in a reaction catalyzed by phenylalanine hydroxylase. Alanine, valine and leucine are each biosynthetic products derived from pyruvate, the final product of glycolysis. Aspartate is formed from oxalacetate, an intermediate product of the citrate cycle. Asparagine, methionine, threonine and lysine are each produced by the conversion of aspartate. Isoleucine is formed from threonine. Histidine is formed from 5-phosphoribosyl 1-pyrophosphate, an activated sugar, in a complex 9-step pathway.

Amounts of amino acids exceeding those required for protein biosynthesis cannot be stored and are instead broken down so that intermediate products are provided for the principal metabolic pathways in the cell (for a review, see Stryer, L., Biochemistry, 3rd edition, Chapter 21 "Amino Acid Degradation and the Urea Cycle"; pp. 495-516 (1988)). Although the cell is able to convert unwanted amino acids into the useful intermediate products of metabolism, production of amino acids is costly in terms of energy, the precursor molecules and the enzymes necessary for their synthesis. It is therefore not surprising that amino acid biosynthesis is regulated by feedback inhibition, whereby the presence of a particular amino acid slows down or completely stops its own production (for a review of feedback mechanism in amino acid biosynthetic pathways, see Stryer, L., Biochemistry, 3rd edition, Chapter 24, "Biosynthesis of Amino Acids and Heme", pp. 575-600 (1988)). The output of a particular amino acid is therefore restricted by the amount of this amino acid in the cell.

B. Metabolism and Uses of Vitamins, Cofactors and Neutracenticals

Vitamins, cofactors and nutraceuticals comprise another group of molecules. Higher animals have lost the ability to synthesize them and therefore have to take them in, although they are easily synthesized by other organisms such as bacteria. These molecules are either bioactive molecules per se or precursors of bioactive substances which serve as electron carriers or intermediate products in a number of metabolic pathways. Besides their nutritional value, these compounds also have a significant industrial value as colorants, antioxidants and catalysts or other processing auxiliaries. (For a review of the structure, activity and industrial applications of these compounds, see, for example, Ullmann's Encyclopedia of Industrial Chemistry, "Vitamins", Vol. A27, pp. 443-613, VCH: Weinheim, 1996). The term "vitamin" is known in the art and comprises nutrients which are required for normal functional of an organism but cannot be synthesized by this organism itself. The group of vitamins may include cofactors and nutraceutical compounds. The term "cofactor" comprises nonproteinaceous compounds necessary for the appearance of a normal enzymic activity. These compounds may be organic or inorganic; the cofactor molecules of the invention are preferably organic. The term “nutraceutical” comprises food additives which are health-promoting in plants and animals, especially humans. Examples of such molecules are vitamins, antioxidants and likewise certain lipids (e.g. polyunsaturated fatty acids).

The biosynthesis of these molecules in organisms able to produce them, such as bacteria, has been comprehensively characterized (Ullmann's Encyclopedia of Industrial Chemistry, “Vitamins”, Vol. A27, pp. 443-613, VCH: Weinheim, 1996, Michal, G. (1999) Biochemical Pathways: An Atlas of Biochemistry and Molecular Biology, John Wiley & Sons; Ong, A. S., Niki, E. and Packer, L. (1995) “Nutrition, Lipids, Health and Disease” Proceedings of the UNESCO/Confederation of Scientific and Technological Associations in Malaysia and the Society for free Radical Research—Asia, held on Sep. 1-3, 1994, in Penang, Malaysia, AOCS Press, Champaign, Ill. X, 374 S).

Thiamine (vitamin $B_1$) is formed by chemical coupling of pyrimidine and thiazole units. Riboflavin (vitamin $B_2$) is synthesized from guanosine 5'-triphosphate (GTP) and ribose 5'-phosphate. Riboflavin in turn is employed for the synthesis of flavin mononucleotide (FMN) and flavin adenine dinucleotide (FAD). The family of compounds together referred to as “vitamin B6” (for example pyridoxine, pyridoxamine, pyridoxal 5'-phosphate and the commercially used pyridoxine hydrochloride), are all derivatives of the common structural unit 5-hydroxy-6-methylpyridine. Panthothenate (pantothenic acid, R-(+)-N-(2,4-dihydroxy-3,3-dimethyl-1-oxobutyl)-β-alanine) can be prepared either by chemical synthesis or by fermentation. The last steps in pantothenate biosynthesis consist of ATP-driven condensation of β-alanine and pantoic acid. The enzymes responsible for the biosynthetic steps for the conversion into pantoic acid and into β-alanine and for the condensation to pantothenic acid are known. The metabolically active form of pantothenate is coenzyme A whose biosynthesis takes place by 5 enzymatic steps. Pantothenate, pyridoxal 5'-phosphate, cysteine and ATP are the precursors of coenzyme A. These enzymes catalyze not only the formation of pantothenate but also the production of (R)-pantoic acid, (R)-pantolactone, (R)-panthenol (provitamin $B_5$), pantetheine (and its derivatives) and coenzyme A.

The biosynthesis of biotin from the precursor molecule pimeloyl-CoA in microorganisms has been investigated in detail, and several of the genes involved have been identified. It has emerged that many of the corresponding proteins are involved in the Fe cluster synthesis and belong to the class of nifS proteins. Liponic acid is derived from octanonoic acid and serves as coenzyme in energy metabolism where it is a constituent of the pyruvate dehydrogenase complex and of the α-ketoglutarate dehydrogenase complex. Folates are a group of substances all derived from folic acid which in turn is derived from L-glutamic acid, p-aminobenzoic acid and 6-methylpterin. The biosynthesis of folic acid and its derivatives starting from the intermediate products of the biotransformation of guanosine 5'-triphosphate (GTP), L-glutamic acid and p-aminobenzoic acid has been investigated in detail in certain microorganisms.

Corrinoids (such as the cobalamines and, in particular, vitamin $B_{12}$) and the porphyrins belong to a group of chemicals distinguished by a tetrapyrrole ring system. The biosynthesis of vitamin $B_{12}$ is so complex that it has not yet been completely characterized, but many of the enzymes and substrates involved are now known. Nicotinic acid (nicotinate) and nicotinamide are pyridine derivatives which are also referred to as “niacin”. Niacin is the precursor of the important coenzymes AND (nicotinamide adenine dinucleotide) and NADP (nicotinamide adenine dinucleotide phosphate) and their reduced forms.

Production of these compounds on the industrial scale is mostly based on cell-free chemical syntheses, although some of these chemicals, such as riboflavin, vitamin $B_6$, pantothenate and biotin, have also been produced by large-scale cultivation of microorganisms. Only vitamin $B_{12}$ is, because of the complexity of its synthesis, produced only by fermentation. In vitro processes require a considerable expenditure of materials and time and frequently high costs.

C. Purine, Pyrimidine, Nucleoside and Nucleotide Metabolism and Uses

Genes for purine and pyrimidine metabolism and their corresponding proteins are important aims for the therapy of oncoses and viral infections. The term “purine” or “pyrimidine” comprises nitrogen-containing bases which form part of nucleic acids, coenzymes and nucleotides. The term “nucleotide” encompasses the fundamental structural units of nucleic acid molecules, which comprise a nitrogen-containing base, a pentose sugar (the sugar is ribose in the case of RNA and the sugar is D-deoxyribose in the case of DNA) and phosphoric acid. The term “nucleoside” comprises molecules which serve as precursors of nucleotides but have, in contrast to the nucleotides, no phosphoric acid unit. It is possible to inhibit RNA and DNA synthesis by inhibiting the biosynthesis of these molecules or their mobilization to form nucleic acid molecules; targeted inhibition of this activity in cancer cells allows the ability of tumor cells to divide and replicate to be inhibited. There are also nucleotides which do not form nucleic acid molecules but serve as energy stores (i.e. AMP) or as coenzymes (i.e. FAD and NAD).

Several publications have described the use of these chemicals for these medical indications, the purine and/or pyrimidine metabolism being influenced (for example Christopherson, R. I. and Lyons, S. D. (1990) “Potent inhibitors of de novo pyrimidine and purine biosynthesis as chemotherapeutic agents”, Med. Res. Reviews 10: 505-548). Investigations of enzymes involved in purine and pyrimidine metabolism have concentrated on the development of novel medicaments which can be used, for example, as immunosuppressants or antiproliferative agents (Smith, J. L. (1995) “Enzymes in Nucleotide Synthesis” Curr. Opin. Struct. Biol. 5: 752-757; (1995) Biochem. Soc. Transact. 23: 877-902). However, purine and pyrimidine bases, nucleosides and nucleotides also have other possible uses: as intermediate products in the biosynthesis of various fine chemicals (e.g. thiamine, S-adenosylmethionine, folates or riboflavin), as energy carriers for the cell (for example ATP or GTP) and for chemicals themselves, which are ordinarily used as flavor enhancers (for example IMP or GMP) or for many medical applications (see, for example, Kuninaka, A., (1996) “Nucleotides and Related Compounds in Biotechnology” Vol. 6, Rehm et al., editors VCH: Weinheim, pp. 561-612). Enzymes involved in purine, pyrimidine, nucleoside or nucleotide metabolism are also increasingly serving as targets against which chemicals are being developed for crop protection, including fungicides, herbicides and insecticides.

The metabolism of these compounds in bacteria has been characterized (for reviews, see, for example, Zalkin, H. and Dixon, J. E. (1992) “De novo purine nucleotide biosynthesis” in Progress in Nucleic Acids Research and Molecular biology, Vol. 42, Academic Press, pp. 259-287; and Michal, G. (1999) "Nucleotides and Nucleosides"; Chapter 8 in : Biochemical Pathways: An Atlas of Biochemistry and Molecular Biology, Wiley, New York). Purine metabolism, the object of intensive research, is essential for normal functioning of the cell. Disordered purine metabolism in higher animals may cause severe illnesses, for example gout. Purine nucleotides are synthesized from ribose 5-phosphate by a number of steps via the intermediate compound inosine 5'-phosphate (IMP), leading to the production of guanosine 5'-monophosphate (GMP) or adenosine 5'-monophosphate (AMP), from which the triphosphate forms used as nucleotides can easily be prepared. These compounds are also used as energy stores, so that breakdown thereof provides energy for many different biochemical processes in the cell. Pyrimidine biosynthesis takes place via formation of uridine 5'-monophosphate (UMP) from ribose 5-phosphate. UMP in turn is converted into cytidine 5'-triphosphate (CTP). The deoxy forms of all nucleotides are prepared in a one-step reduction reaction from the diphosphate ribose form of the nucleotide to give the diphosphate deoxyribose form of the nucleotide. After phosphorylation, these molecules can take part in DNA synthesis.

D. Trehalose Metabolism and Uses

Trehalose consists of two glucose molecules linked together by an α,α-1,1 linkage. It is ordinarily used in the food industry as sweetener, as additive for dried or frozen foods and in beverages. However, it is also used in the pharmaceutical industry or in the cosmetics industry and biotechnology industry (see, for example, Nishimoto et al., (1998) U.S. Pat. No. 5,759,610; Singer, M. A. and Lindquist, S. (1998) Trends Biotech. 16: 460-467; Paiva, C. L. A. and Panek, A. D.(1996) Biotech Ann. Rev. 2: 293-314; and Shiosaka, M. (1997) J. Japan 172: 97-102). Trehalose is produced by enzymes of many microorganisms and is naturally released into the surrounding medium from which it can be isolated by methods known in the art.

II. Genetic Stability, Protein Synthesis and Protein Secretion in *C. glutamicum*

The production of a compound of interest from a cell such as *C. glutamicum* is the culmination of a large number of separate processes which are nevertheless linked to one another and each of which is crucial for the overall production and release of said compound from the cell. When modifying a cell for it to overproduce one or more chemicals, each of these processes must be taken into account in order to ensure that the biochemical machinery of the cell is compatible with this genetic manipulation. Particularly important cellular mechanisms include the stability of the modified gene(s) when introduced into the cell, the ability of the mutated gene to be transcribed and translated correctly (including codon usage) and the ability of the mutated protein product to be folded and/or secreted correctly.

A. Bacterial Repair and Recombination Systems

Cells are constantly exposed to nucleic-acid damaging agents such as UV irradiation, oxygen-free radicals and alkylation. Furthermore, even the action of DNA polymerases is not free of errors. The cells must maintain an equilibrium between genetic stability (which ensures that genes required for cellular functions are not damaged during normal growth and metabolism) and genetic variability (which makes it possible for the cells to adapt to a changing environment). Therefore, most cells contain separate pathways for DNA repair and DNA recombination, which are, however, connected to one another. The former serves to strictly correct errors in DNA molecules either by directly reverting the damage or by excising the damaged region and replacing it with the correct sequence. The latter recombination system also repairs nucleic acid molecules, but only the damage which causes damage in both DNA strands so that it is not possible to use any strand as a template for correcting the other one. Recombination repair and SOS reaction may readily lead to inversions, deletions or other genetic rearrangements within or around the damaged region, and this in turn promotes a certain degree of genomic instability which may contribute to the ability of the cell to adapt to changing environments or to stress.

High-fidelity repair mechanisms include the direct reversal of the DNA damage and excision of said damage and resynthesis using the information encoded in the complementary strand. The direct reversal of said damage requires an enzyme having an activity which causes the opposite of what originally damaged the DNA. For example, the action of DNA-repair methyltransferases can correct incorrect DNA methylation and the activity of deoxyribodipyrimidine photolyase can repair nucleotide dimers generated by UV irradiation by cleaving said dimer again into the corresponding nucleotides in the presence of light (see Michal, G. (1999) Biochemical Pathways: An Atlas of Biochemistry and Molecular Biology, Wiley: New York, and the references therein).

Accurate repairing of large damage requires specialized repair mechanisms. These include the mismatch repair and excision repair systems. The damage to an individual base can be corrected by a number of cleavage reactions, with the sugar bond being cleaved first, followed by cleavage of the DNA backbone at the damaged site and removal of the damaged base itself. Finally, DNA polymerase and DNA ligase fill in and close the gap by using the second DNA strand as template. A more substantial DNA damage which leads to a modified conformation of the double helix is corrected by the ABC system in which helicase II, DNA polymerase I, the UvrA, UvrB and UvrC proteins together cleave a single strand of the double helix at the damaged site, unwind the damaged region in an ATP-dependent manner, excise the damaged region and fill in the missing region using the other strand as template. Finally, DNA ligase closes the single-strand break. There are also specific repair systems for G-T mismatches (in which systems the Vsr protein is involved) and for minor deletion/insertion errors owing to erroneous repair of the two strands (in which systems the methylation-controlled pathway is involved).

There are also low-fidelity repair systems which are usually used for correcting very extended DNA damage in bacteria. Double-strand repair and recombination are carried out in the case of damage which affects both DNA strands. It is impossible in this situation to repair the damage by using the other strand as template. Thus, the repair system includes a double-crossover event between the damaged region and another copy of the region on a homologous DNA molecule. This is possible, since bacteria divide so rapidly that a second copy of the genomic DNA is usually available, before cell division actually takes place. Said crossover event may readily lead to inversions, duplications, deletions, insertions and other genetic rearrangements and thus overall increases the genetic instability of the organism.

The SOS reaction is activated if the damage in the DNA is sufficient for DNA polymerase III to stop and not be able to continue replication. Under these circumstances, single-stranded DNA is present. RecA protein is activated by binding to single-stranded DNA, and this activated form leads to activation of the LexA repressor, thereby removing the transcriptional block of more than 20 genes, including UvrA, UvrB, UvrC, helicase II, DNA pol III, UmuC and UmuD. The combined activities of these enzymes fill in the gap region sufficiently for DNA pol III to continue replication. However, these gaps are filled with bases which should not be present; thus, this type of repair leads to error-prone repair and this overall contributes to genetic instability in the cell.

B. Transposons

The abovementioned high- or low-fidelity systems ought to repair DNA damage. Under certain circumstances, this repair may include additional gene rearrangements. Moreover, many bacterial cells have mechanisms which ought to specifically cause such gene rearrangements. Particularly well known examples of such mechanisms are the transposons.

Transposons are genetic elements which can migrate from one site to another, either within a chromosome or between a piece of extrachromosomal DNA (e.g. a plasmid) and a chromosome. The transposition may be carried out in several ways; for example, the transposable element may be excised from the donor site and integrated into the target site (nonreplicative transposition) or, as an alternative, the transposable element may be copied from the donor site to the target-site, resulting in two copies of said element (replicative transposition). The sequences of the donor site and the target site are usually not related.

Said transposition event has a multiplicity of possible results. Integration of a transposable element into a gene disrupts said gene, and this normally completely eliminates the function of said gene. An integration event which takes place in the DNA surrounding said gene cannot interfere with the coding sequence itself but may have a fundamental effect on the regulation of said gene and thus on its expression. Recombination events between two copies of a transposable element which is located in different sections of the genome may lead to deletions, duplications, inversions, transpositions or amplifications of segments of the genome. It is also possible for various replicons to fuse.

The simplest transposon-like genetic elements are referred to as insertion (IS) elements. IS elements contain a nucleotide region of variable length (but usually less than 1500 bases) which contains no coding regions and is on each end surrounded by inverted repeats. Since the IS element does not encode any proteins whose activity can be detected, the presence of an IS element is usually observed only due to the loss of function of one or more genes into which the IS element has been inserted.

Transposons are mobile genetic elements which, in contrast to IS elements, contain nucleic acid sequences which are bordered by repeats and may encode one or more proteins. It is not unusual for these repeat regions to comprise IS elements. The transposon-encoded proteins are usually transposases (proteins which catalyze migration of the transposon from one site to another) and antibiotic resistance genes. The mechanisms and regulation of the transposable elements are known in the art and have been described, at least by way of example, in: Lengeler et al. (1999) Biology of Prokaryotes, Thieme Verlag: Stuttgart, pp. 375-361; Neidhardt et al. (1996) *Escherichia coli* and *Salmonella,* ASM Press: Washington, D.C.; Sonenshein, Al. L., et al., Editors, (1993) *Bacillus subtilis,* ASM Press, Washington, D.C.; Voet, D., and Voet, J. G. (1992) Biochemie, VCH: Weinheim, pp. 985-990; Brock, T. D., and Madigan, M. T. (1991) Biology of Mocroorganisms, 6th edition, Prentice Hall: New York,. pp. 267-269; and Kleckner, N. (1990) "Regulation of transposition in bacteria", Annu. Rev. Biochem. 61:297-327.

C. Transcription

The expression of genes in bacteria is regulated mainly at the level of transcription. The transcriptional apparatus comprises a number of proteins which can be divided into two groups: RNA polymerase (the operating DNA-transcribing enzyme) and sigma factors (which regulate gene transcription by directing RNA polymerase to specific promoter DNA sequences which recognize said factors). The combination of RNA polymerase and sigma factors generates the RNA-polymerase holoenzyme, an activated complex. Gram-positive bacteria such as *Corynebacteria* contain only one type of RNA polymerase but a number of different sigma factors which are specific for various promoters, growth phases, environmental conditions, substrates, oxygen levels, transport processes and the like, and, as a result, the organism can adapt to various environmental and metabolic conditions.

Promoters are specific DNA sequences which serve as docking sites for the RNA-polymerase holoenzyme. Many promoter elements have conserved sequence elements which can be detected by homology searching; as an alternative, promoter regions for a particular gene may be identified using standard techniques such as primer extension. Many promoter regions of Gram-positive bacteria are known (see, for example, Sonenshein, A. L., Hoch, J. A., and Losick, R., Editors, (1993) *Bacillus subtilis,* ASM Press: Washington, D.C.).

A plurality of repressing or activating mechanisms influence the transcriptional control of the promoter. Specific regulatory proteins which bind to promoters are capable of blocking (repressors) or supporting (activators) binding of the RNA holoenzyme and thus regulating transcription. Binding of these repressor and activator molecules is in turn regulated by their interactions with other molecules such as proteins or other metabolic compounds. As an alternative, transcription may be regulated by factors which influence processes such as elongation or termination (see, for example, Sonenshein, A. L., Hoch, J. A., and Losick, R., Editors, (1993) *Bacillus subtilis,* ASM Press: Washington, D.C.). The ability to regulate the transcription of genes as a reaction to a multiplicity of environmental or metabolic signals enables the cells to control exactly when a gene can be expressed and how much gene product can be present in the cell at a point in time. This in turn prevents unnecessary wasting of energy or the unnecessary use of possibly rare intermediates or cofactors.

D. Translation and Aminoacyl-tRNA Synthetases

Translation is the process which synthesizes a polypeptide from amino acids according to the information contained in an RNA molecule. The major components of this process are ribosomes and specific initiation or elongation factors, such as IF1-3, INVENTIVE-G and EFTu (see, for example, Sonenshein, A. L., Hoch, J. A., and Losick, R., Editors, (1993) *Bacillus subtilis,* ASM Press: Washington, D.C.).

Each codon of the mRNA molecule encodes a particular amino acid. mRNA is converted into amino acid via transfer-RNA (tRNA) molecules. These molecules consist of an RNA single strand (between 60 and 100 bases) which is present in a L-shaped three-dimensional structure with extending regions or "arms". One of these arms forms base pairs with a particular codon sequence on the mRNA molecule. A second arm interacts specifically with a particular amino acid (which is encoded by the codon). Other tRNA arms include the variable arm, the TΨC arm (which carries thymidylate and pseudouridylate modifications) and the D arm (which carries a dihydrouridine modification). The function of said latter structures is still unknown, but their conservation among the tRNA molecules suggests a role in protein synthesis.

A family of enzymes which are referred to as aminoacyl-tRNA synthetases must act in order for the nucleic acid-based tRNA molecule to pair with the correct amino acid. There is a large variety of these enzymes and each of them is specific for a particular tRNA and a particular amino acid. Said enzymes bind the 3'-hydroxyl of the terminal tRNA-adenosin-ribose unit to the amino acid in a two-step reaction. Firstly, the enzyme is activated via reaction with ATP and the amino acid, resulting in an aminoacyl-tRNA-synthetase-aminoacyl-adenylate complex. Secondly, the aminoacyl group is transferred from the enzyme to the target tRNA on which it remains in a high-energy state. Binding of the tRNA molecule to its recognition codon on the mRNA molecule then contacts the tRNA-bound high energy amino acid with the ribosome. Within the ribosome, the amino acid-loaded tRNA (aminoacyl tRNA) occupies a binding site (the A site) beside a second site (the P site) which carries a tRNA molecule whose amino acid is bound to the nascent polypeptide chain (peptidyl tNRA). The activated amino acid on the aminoacyl tRNA is sufficiently reactive for a peptide bond to form spontaneously between this amino acid and the next amino acid on the nascent polypeptide chain. GTP hydrolysis provides the energy for transferring the tRNA which is now loaded with the polypeptide chain from the A site to the p site of the ribosome, and this process is repeated until it reaches a stop codon.

There is a number of different steps at which translation can be regulated. These steps include binding of the ribosome to mRNA, the presence of mRNA secondary structure, the codon usage or the frequency of particular tRNAs. Specific regulatory mechanisms such as attenuation, too, may act at the translational level. An in-depth overview over many of these mechanisms can be found, for example, in Vellanoweth, R. L. (1993) "Translation and its Regulation", in: *Bacillus subtilis* and other Gram Positive Bacteria, Sonenshein, A. L., et al., Editors, ASM Press: Washington, D.C., pp. 699-711 and the references cited therein.

E. Protein Folding and Protein Secretion

Ribosomal synthesis of proteins leads to polypeptide chains which must adopt a three-dimensional form before the protein can function normally. The three-dimensional structure is achieved by a folding process. Polypeptide chains are flexible and (in principle) move readily and freely in solution until they adopt a conformation which leads to a more stable three-dimensional structure. Sometimes, however, it is difficult for proteins to fold correctly, either due to the environmental conditions (e.g. high temperature at which the kinetic energy present in the system makes it more difficult for the protein to reach the energy minimum of a stable structure) or due to the type of the protein itself (for example, hydrophobic regions in proteins closely located to one another tend to aggregate, thereby precipitating themselves from aqueous solutions).

Protein-like factors have been identified which can catalyze, accompany or otherwise support the folding of proteins and which are synthesized co- or posttranslationally. These protein-folding molecules include the prolyl-peptidyl isomerases (e.g. trigger factor, cyclophilin and FKBP homologs) and also proteins of the group of heat shock proteins (e.g. DnaK, DnaJ, GroEL, small heat shock proteins, HtpG and members of the Clp family (e.g. ClpA, ClpB, ClpW, ClpP and ClpX). Many of these proteins are important for the viability of cells: in addition to their function in protein folding, protein translocation and protein processing, they frequently serve as targets for the overall regulation of protein synthesis (see, for example, Bukau, B. (1993) Molecular Microbiology 9(4):671-680; Bukau, B., and Horwich, A. L. (1998) Cell 92(3):351-366; Hesterkamp, T., Bukau, C. (1996) FEBS Lett. 389(l):32-34; Yaron, A., Naider, F. (1993) Critical Reviews in Biochemistry and Molecular Biology 28(1):31-81; Scheibel, R., Buchner, J. (1998) Biochemical Pharmacology 56(6):675-682; Ellis, R. J., Hartl, F. U. (1996) FASEB Journal 10(1):20-26; Wawrzynow, A., et al. (1996) Molecular Microbiology 21(5):895-899; Ewalt, K. L., et al. (1997) Cell 90(3):491-500).

The chaperones identified previously act in two ways: they either bind to and stabilize polypeptides or provide an environment in which folding can take place without disruption. The former group, including, for example, DnaK, DnaJ and the heat shock proteins, binds directly to the nascent or wrongly folded polypeptide, frequently accompanied by ATP hydrolysis. Binding of the chaperone prevents the polypeptide from aggregating with other polypeptides and can force dissolution of these aggregates if they have already formed. After interaction with a second chaperone GrpE (which makes it possible for an ADP-ATP exchange to take place), the polypeptide is released in the molten-globule state and is able to fold. If the folding is wrong, the chaperones rebind to the wrongly folded protein and force its return to an unfolded state. This cycle can be repeated until the protein is correctly folded. In contrast to the first group of chaperones which simply bind to the polypeptide, the second group (e.g. GroEL/ES) not only binds to the polypeptide but encloses it completely so that it is protected from the environment. The GroEL/ES complex consists of two stacked 14-membered rings with a hydrophobic inner surface and a "lid" made of a 7-membered ring. In an ATP-dependent reaction, the polypeptide is drawn into the channel in the center of this complex, where it can fold without disruption by other polypeptides. Wrongly folded proteins are not released from the complex.

An important step in protein folding is the formation of disulfide bonds. These bonds, either within a subunit or between subunits of proteins, are important for protein stability. Disulfide bonds form readily in aqueous solution, and it is difficult to reverse a wrong disulfide bridge formation without the aid of a reducing environment. In order to support this process of correct disulfide bridge formation, the cytosol of most cells contains thiol-containing molecules such as glutathion or thioredoxin and their corresponding oxidation/reduction systems (Loferer, H., Hennecke, H. (1994) Trends in Biochemical Sciences 19(4):169-171).

At certain times, however, the folding of nascent polypeptide chain is not desirable, for example if these proteins are to be secreted. The folding process usually results in the hydrophobic regions of the protein being located in the center of said protein, removed from the aqueous solution, and the hydrophilic regions being presented on the outer surfaces of said protein. Although this conformation arrangement generates higher stability for the protein, it makes translocation of the protein via membranes more difficult, since the hydrophobic core of the membrane is per se incompatible with the hydrophilic exterior of the protein. Thus, the proteins synthesized by the cell, which have to be secreted to the exterior of the cell (e.g. cell surface enzymes and membrane receptors) or which have to be inserted into the membrane itself (e.g. transporter proteins and channel proteins) are usually secreted or inserted prior to folding. The same chaperones which prevent the aggregation of nascent polypeptide chains also prevent folding of polypeptides, until they are no longer needed. Thus, these proteins can "escort" nascent polypeptide chains to a suitable location in the cell, where they either are removed so as to enable folding or transfer the protein to a transport system which either secretes the polypeptide or supports its insertion into a membrane.

During the course of evolution, a specialized protein machinery has formed, which recognizes, binds, transports and processes proteins with specific prosequences (which are later removed from the protein by cleavage). Said machinery comprises a number of proteins which are collectively referred to as sec (type II secretion) system (for an overview, see Gilbert, M., et al. (1995) Critical Reviews in Biotechnology 15(1):13-39 and references therein; Freudl, R. (1992) Journal of Biotechnology 23(3):231-240 and references therein; Neidhardt, F. C., et al. (1996) *E. coli* and *Salmonella,* ASM Press: Washington, D.C., pp. 967-978; Binet, R., et al. (1997) Gene 192(1):7.-11 und Rapoport, T. A. (1986) Critical Reviews in Biochemistry 20(1):73-137 and references therein). The sec system comprises chaperones (e.g. SecA and SecB), integral membrane proteins which are also referred to as translocases (e.g. SecY, SecE and SecG) and signal peptidases (e.g. LepB). The nascent polypeptide with a prosequence leading to secretion is bound by SecB which transfers it to SecA on the inner surface of the cell membrane. SecA binds to the prosequence and, after ATP hydrolysis, inserts into the membrane and also forces part of the polypeptide through the membrane. The rest of the polypeptide is led through the membrane via a complex of translocases such as SecY, SecE and SecG. Finally, the signal peptidase removes the prosequence by cleavage and the polypeptide is located freely on the extracellular side of the membrane, where it folds spontaneously.

Sec-independent secretory mechanisms are also known. For example, the signal recognition particle-dependent pathway comprises binding of a signal recognition particle (SRP) protein to the nascent polypeptide during its synthesis, thereby stopping the ribosome. A receptor for SRP on the inner surface of the membrane then binds the ribosome-polypeptide-SRP complex. GTP hydrolysis provides the energy required for transferring the complex to the sec-translocase complex on which the polypeptide is led across the membrane during its synthesis by the ribosome. It is known that other secretory mechanisms exist, which are specific for only a few proteins.

III. Elements and Methods of the Invention

The present invention is based, at least partially, on the detection of new molecules which are referred to herein as SES nucleic-acid and SES-protein molecules and which take part in the repair or recombination of DNA in *C. glutamicum,* transposition or other rearrangement of *C. glutamicum* DNA, gene expression in *C. glutamicum* (i.e. transcriptional or translational processes), protein-folding or protein secretion of this microorganism. In one embodiment, the SES molecules take part in the repair or recombination of DNA, transposition of genetic material, gene expression (i.e. transcriptional or translational processes), protein folding or protein secretion in *Corynebacterium glutamicum.* In a preferred embodiment, the activity of the SES molecules of the invention affects the production of a fine chemical of interest by said microorganism with regard to the repair or recombination of DNA, transposition of DNA, gene expression, protein folding or protein secretion. In a particularly preferred embodiment, the activity of the SES molecules of the invention is modulated such that the activity of the cellular processes of *C. glutamicum,* in which the SES proteins of the invention are involved, (e.g. repair or recombination of DNA, transposition of DNA, gene expression, protein folding or protein secretion), is also modified, and this results directly or indirectly in a modulation of the yield, production and/or efficiency of production of a fine chemical of interest by *C. glutamicum.*

The term "SES protein" or "SES polypeptide" comprises proteins which are involved in a number of cellular processes which are related to genetic stability, gene expression, protein folding or protein secretion of *C. glutamicum.* For example, an SES protein may be involved in the DNA repair or in recombination mechanisms in *C. glutamicum,* in rearrangements of the genetic material of *C. glutamicum* (such as those mediated by transposons), in the transcription or translation of genes in this microorganism, in mediating protein folding in *C. glutamicum* (such as the activity of chaperones) or in the secretion of proteins from *C. glutamicum* cells (e.g. on the sec system). Examples of SES proteins comprise those which are encoded by the SES genes listed in Table 1 and Appendix A. The terms "SES gene" or "SES nucleic acid sequence" comprise nucleic acid sequences encoding an SES protein which comprises a coding region and corresponding untranslated 5' and 3' sequence regions. Examples of SES genes are those listed in Table 1. The terms "production" or "productivity" are known in the art and include the concentration of the fermentation products (for example of the fine chemical of interest, which is produced within a predetermined time interval and a predetermined fermentation volume (e.g. kg of product per h per l)). The term "efficiency of production" comprises the time required by the cell for reaching a particular production quantity (for example, the time required by the cell for reaching a particular output rate of a fine chemical). The term "yield" or "product/carbon yield" is known in the art and comprises the efficiency of converting the carbon source into the product (i.e. the fine chemical). This is, for example, usually expressed as kg of product per kg of carbon source. Increasing the yield or production of the compound increases the amount of the molecules obtained or of the suitable obtained molecules of this compound in a particular culture volume over a predetermined period. The terms "biosynthesis" or "biosynthetic pathway" are known in the art and comprise the synthesis of a compound, preferably an organic compound, from intermediates by a cell, for example in a multistep process or highly regulated process. The terms "degradation" and "degradation pathway" are known in the art and comprise cleavage of a compound, preferably an organic compound, into degradation products (in more general terms: smaller or less complex molecules) by a cell, for example in a multistep process or highly regulated process. The term "metabolism" is known in the art and comprises the entirety of biochemical reactions which take place in an organism. The metabolism of a particular compound (e.g. the metabolism of an amino acid such as glycine) then comprises all biosynthetic, modification and degradation pathways in the cell, which relate to said compound. The term "DNA repair" is known in the art and includes cellular mechanisms by which the errors in the DNA (either due to damage such as, but not limited to, ultraviolet radiation, methylases, low-fidelity replication or mutagens) are excised and corrected. The term "recombination" or "DNA recombination" is known in the art and comprises cellular mechanisms which correct extended DNA damage which affects both strands of a DNA molecule via homologous recombination with another undamaged copy of the DNA molecule within the same cell. These repairs are usually of low fidelity and may result in gene rearrangements. The term "transposon" is known in the art and comprises a DNA element which can insert randomly into the genome of an organism and may result in the disruption of genes or their regulatory regions or in duplications, inversions, deletions and other gene arrangements. The term "protein folding" is known in the art and comprises the migration of a polypeptide chain through several three-dimensional configurations until the stable active three-dimensional configuration is attained. The formation of disulfide bonds and sequestering of hydrophobic region from the surrounding aqueous solution provides some of the driving forces for this protein folding process and correct folding can be enhanced by the activity of chaperones. The terms "secretion" or "protein secretion" are known in the art and comprise the movement of proteins from the cell interior to the cell exterior in a mechanism in which a system of secretory proteins enables their passage via the cell membrane to the cell exterior.

In another embodiment, the SES molecules of the invention are able to modulate the production of a molecule of interest, such as a fine chemical, in a microorganism such as *C. glutamicum*. There is a number of mechanisms by which modification of an SES protein of the invention can directly influence the yield, production and/or efficiency of production of a fine chemical from a *C. glutamicum* strain containing this modified protein. For example, modulation of proteins directly involved in transcription or translation (e.g. polymerases or ribosomes) so as to increase their number or activity should overall increase cellular transcription or translation (or the rate of these processes). This increased cellular gene expression should include those proteins which are involved in the biosynthesis of fine chemicals so that the yield, production or efficiency of production of one or more compounds of interest can be increased. Modifications of the transcriptional/translational protein machinery of *C. glutamicum* so as to modify regulation of these proteins may also enable the increased expression of genes involved in the production of fine chemicals. Modulation of the activity of a number of proteins involved in peptide folding may increase the overall production of correctly folded molecules in the cell, thereby increasing the possibility of proteins of interest (e.g. proteins of the biosynthesis of fine chemicals) functioning correctly. Furthermore, it may be possible, by mutating proteins involved in the secretion from *C. glutamicum* so as to increase their number or activity, to increase secretion of a fine chemical (e.g. an enzyme) from cells in a fermentative culture from which said fine chemical can be readily obtained.

Genetic modification of the SES molecules of the invention may also modulate indirectly the production of one or more fine chemicals. For example, it is possible, by increasing the number or activity of a DNA-repair or DNA-recombination protein of the invention, to increase the ability of the cell to detect and repair DNA damage. This should effectively increase the ability of the cell to keep a mutated gene in its genome and thereby increase the probability of a transgene genetically introduced into *C. glutamicum* (which encodes, for example, a protein which increases the biosynthesis of a fine chemical) not being lost during cultivation of the microorganism. In contrast, it may be possible, by reducing the number or activity of one or more DNA-repair or DNA-recombination proteins, to increase the genetic instability of the organism. These manipulations should improve the ability of said organism to be modified by mutagenesis, without correcting the introduced mutation. The same is true for proteins which are involved in the transposition or rearrangement of genetic elements in *C. glutamicum* (e.g. transposons). Mutagenesis of these proteins so as to either increase or reduce their number or activity makes it possible to increase or reduce at the same time the genetic stability of the microorganism. This crucially affects the possibility of introducing another mutation into *C. glutamicum* and of retaining the introduced mutation. Transposons likewise provide a suitable mechanism which makes possible the mutagenesis of *C. glutamicum;* duplication of genes of interest (e.g. genes of the biosynthesis of fine chemicals) as well as disruption of unwanted genes (e.g. genes involved in the degradation of fine chemicals of interest) can be readily carried out by means of transposon mutagenesis.

It may be possible, by modulating one or more proteins (e.g. sigma factors) which are involved in the regulation of transcription or translation in reaction to particular environmental conditions, to prevent the cell from slowing down or stopping protein synthesis under unfavorable environmental conditions as found in a large-scale fermentative culture. This should increase gene expression, and this in turn may enable the increased biosynthesis of fine chemicals of interest under said conditions. Many of these secreted proteins have functions which are important for cell viability (e.g. cell surface proteases or cell surface receptors). Changing the secretion pathway so that said proteins are transported more easily to their extracellular location may increase the overall viability of the cell and thus result in higher numbers of *C. glutamicum* cells which are able to produce fine chemicals during a large-scale cultivation. Since it is furthermore known that particular bacterial protein secretion pathways (e.g. the sec system) are also involved in the insertion of integral membrane proteins (e.g. receptors, channels, pores, or transporters) into the membrane, modulating the activity of proteins involved in protein secretion from *C. glutamuicum* may affect the ability of the cell to eliminate waste products or to import necessary metabolites. If the activity of these secretory proteins is increased, the ability of the cell to produce fine chemicals (due to an increased presence of transporters/channels in the membrane, which can import nutrients or eliminate waste products) may likewise be increased. If the activity of said secretory proteins is reduced, it may be possible that there are not enough nutrients for supporting the overproduction of compounds of interest or that waste products interfere with this biosynthesis.

A suitable starting point for preparing the nucleic acid sequences of the invention is the genome of a *Corynebacterium glutamicum* strain which can be obtained from the American Type Culture Collection under the name ATCC 13032.

The nucleic acid sequences of the invention can be prepared from these nucleic acid sequences via the modifications denoted in Table 1, using conventional methods.

The SES protein of the invention or a biologically active section or fragment thereof may take part in the repair or recombination of DNA, transposition of genetic material, gene expression (i.e. transcriptional or translational processes), protein folding or protein secretion in *Corynebacterium glutamicum* or have one or more of the activities described in table 1.

The following subsections describe various aspects of the invention in more detail:

A. Isolated Nucleic Acid Molecules

One aspect of the invention relates to isolated nucleic acid molecules which encode SES polypeptides or biologically active sections thereof and to nucleic acid fragments which are sufficient for the use as hybridization probes or primers for identifying or amplifying. SES-encoding nucleic acids (e.g. SES DNA). The term “nucleic acid molecule”, as used herein, is intended to comprise DNA molecules (e.g. cDNA or genomic DNA) and RNA molecules (e.g. mRNA) and also DNA or RNA analogs generated by means of nucleotide analogs. Moreover, this term comprises the untranslated sequence located at the 3' and 5' ends of the coding gene region: at least about 100 nucleotides of the sequence upstream of the 5' end of the coding region and at least about 20 nucleotides of the sequence downstream of the 3' end of the coding region of the gene. The nucleic acid molecule may be single-stranded or double-stranded but is preferably a double-stranded DNA. An “isolated” nucleic acid molecule is removed from other nucleic acid molecules which are present in the natural source of the nucleic acid. An “isolated” nucleic acid preferably does not have any sequences which flank the nucleic acid naturally in the genomic DNA of the organism from which the nucleic acid originates (for example sequences located at the 5' or 3' end of the nucleic acid). In various embodiments, the isolated SES nucleic acid molecule may have, for example, less than about 5 kb, 4 kb, 3 kb, 2 kb, 1 kb, 0.5 kb or 0.1 kb of the nucleotide sequences which naturally flank the nucleic acid molecule in the genomic DNA of the cell from which the nucleic acid originates (e.g. a *C. glutamicum* cell). In addition to this, an “isolated” nucleic acid molecule such as a cDNA molecule may be essentially free of another cellular material or culture medium, if prepared by recombinant techniques, or free of chemical precursors or other chemicals, if synthesized chemically.

A nucleic acid molecule of the invention, for example a nucleic acid molecule having a nucleotide sequence of Appendix A or a section thereof, may be prepared by means of molecular biological standard techniques and the sequence information provided here. For example, a *C. glutamicum* SES cDNA may be isolated from a *C. glutamicum* bank by using a complete sequence from Appendix A or a section thereof as hybridization probe and by using standard hybridization techniques (as described, for example, in Sambrook, J., Fritsch, E. F. and Maniatis, T. Molecular Cloning: A Laboratory Manual. 2nd Ed., Cold Spring Harbor Laboratory, Cold Spring Harbor Laboratory Press, Cold Spring Harbor, N.Y., 1989). Moreover, a nucleic acid molecule comprising a complete sequence from Appendix A or a section thereof can be isolated via polymerase chain reaction, using the oligonucleotide primers produced on the basis of said sequence (for example, it is possible to isolate a nucleic acid molecule comprising a complete sequence from Appendix A or a section thereof via polymerase chain reaction by using oligonucleotide primers which have been produced on the basis of this same sequence of Appendix A). For example, mRNA can be isolated from normal endothelial cells (for example via the guanidinium thiocyanate extraction method of Chirgwin et al. (1979) Biochemistry 18: 5294-5299), and the cDNA can be prepared by means of reverse transcriptase (e.g. Moloney-MLV reverse transcriptase, available from Gibco/BRL, Bethesda, Md., or AMV reverse transcriptase, available from Seikagaku America, Inc., St. Petersburg, Fla.). Synthetic oligonucleotide primers for amplification via polymerase chain reaction can be produced on the basis of any of the nucleotide sequences shown in Appendix A. A nucleic acid of the invention may be amplified by means of cDNA or, alternatively, genomic DNA as template and of suitable oligonucleotide primers according to PCR standard amplification techniques. The nucleic acid amplified in this way may be cloned into a suitable vector and characterized by DNA sequence analysis. Oligonucleotides corresponding to an SES nucleotide sequence may furthermore be prepared by standard syntheses using, for example, an automatic DNA synthesizer.

In a preferred embodiment, an isolated nucleic acid molecule of the invention comprises one of the nucleotide sequences listed in Appendix A.

In a further preferred embodiment, an isolated nucleic acid molecule of the invention comprises a nucleic acid molecule complementary to any of the nucleotide sequences shown in Appendix A or a section thereof, said nucleic acid molecule being sufficiently complementary to any of the nucleotide sequences shown in Appendix A for it to hybridize with any of the sequences indicated in Appendix A, resulting in a stable duplex.

In one embodiment, the nucleic acid molecule of the invention encodes a protein or a section thereof comprising an amino acid sequence which is sufficiently homologous to an amino acid sequence of Appendix B for the protein or a section thereof to retain the ability to take part in the repair or recombination of DNA, transposition of genetic material, gene expression (i.e. transcriptional or translational processes), protein folding or protein secretion in *Corynebacterium glutamicum*. The term “sufficiently homologous”, as used herein, relates to proteins or sections thereof whose amino acid sequences have a minimum number of identical or equivalent amino acid residues (for example an amino acid residue having a side chain similar to that of an amino acid residue in any of the sequences of Appendix B) compared to an amino acid sequence of Appendix B so that the protein or a section thereof is able to take part in the repair or recombination of DNA, transposition of genetic material, gene expression (i.e. transcriptional or translational processes), protein folding or protein secretion in *Corynebacterium glutamicum*. Proteins involved in genetic stability, gene expression, protein folding or protein secretion of *C. glutamicum*, as described herein, may play a part in the production and secretion of one or more fine chemicals. Examples of these activities are likewise described herein. Thus the “function of an SES protein” contributes directly or indirectly to the yield, production and/or efficiency of production of one or more fine chemicals. Table 1 shows examples of SES proteins.

Sections of proteins encoded by the SES nucleic acid molecules of the invention are preferably biologically active sections of any of the SES proteins. The term “biologically active section of an SES protein”, as used herein, is intended to comprise a section, for example a domain/a motif, of an SES protein, which takes part in the repair or recombination of DNA, transposition of genetic material, gene expression (i.e. transcriptional or translational processes), protein folding or protein secretion in *Corynebacterium glutamicum* or has any of the activities depicted in table 1. In order to determine whether an SES protein or a biologically active section thereof is able to take part in the repair or recombination of DNA, transposition of genetic material, gene expression (i.e. transcriptional or translational processes), protein folding or protein secretion in *Corynebacterium glutamicum*, an enzyme activity assay may be carried out.

These assay methods, as described in detail in example 8 of the examples, are familiar to the skilled worker.

In addition to naturally occurring variants of the SES sequence, which may exist in the population, the skilled worker is likewise aware of the fact that changes may be introduced into a nucleotide sequence of Appendix A by mutation, resulting in a change in the amino acid sequence of the encoded SES protein without impairing the functionality of said SES protein. It is possible, for example, to produce in a sequence of Appendix A nucleotide substitutions which result in amino acid substitutions at "nonessential" amino acid residues. A "nonessential" amino acid residue is a residue which can be modified in the wild-type sequence of any of the SES proteins (Appendix B) without modifying the activity of said SES protein, whereas an "essential" amino acid residue is required for SES-protein activity. However, other amino acid residues (e.g. nonconserved or merely semiconserved amino acid residues in the domain with SES activity) may not be essential for activity and thus can probably be modified without modifying SES activity.

An isolated nucleic acid molecule encoding an SES protein which is homologous to a protein sequence of Appendix B may be generated by introducing one or more nucleotide substitutions, additions or deletions into a nucleotide sequence of Appendix A so that one or more amino acid substitutions, additions or deletions are introduced into the encoded protein. The mutations may be introduced into any of the sequences of Appendix A by standard techniques such as site-directed mutagenesis and PCR-mediated mutagenesis. Preference is given to introducing conservative amino acid substitutions at one or more of the predicted nonessential amino acid residues. A "conservative amino acid substitution" replaces the amino acid residue by an amino acid residue with a similar side chain. Families of amino acid residues with similar side chains have been defined in the art. These families comprise amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine), nonpolar side chains (e.g. alanine, valine, leucine, isoleucine, proline, phenylalanine, methionine, tryptophan), beta-branched side chains (e.g. threonine, valine, isoleucine) and aromatic side chains (e.g. tyrosine, phenylalanine, tryptophan, histidine). A predicted nonessential amino acid residue in an SES protein is thus preferably replaced by another amino acid residue of the same side-chain family. In a further embodiment, the mutations may alternatively be introduced randomly over the entire or over part of the SES-encoding sequence, for example by saturation mutagenesis, and the resulting mutants may be tested for an SES activity described herein in order to identify mutants maintaining SES activity. After mutagenesis of any of the sequences of Appendix A, the encoded protein may be expressed recombinantly, and the activity of said protein may be determined, for example, using the assays described herein (see example 8 of the examples).

B. Recombinant Expression Vectors and Host Cells

A further aspect of the invention relates to vectors, preferably expression vectors, containing a nucleic acid which encodes an SES protein (or a section thereof). The term "vector" as used herein, relates to a nucleic acid molecule capable of transporting another nucleic acid to which it is bound. One type of vector is a "plasmid" which term means a circular double-stranded DNA loop into which additional DNA segments can be ligated. Another type of vector is a viral vector, and here additional DNA segments can be ligated into the viral genome. Certain vectors are capable of replicating autonomously in a host cell into which they have been introduced (for example bacterial vectors with bacterial origin of replication and episomal mammalian vectors). Other vectors (e.g. nonepisomal mammalian vectors) are integrated into the genome of a host cell when introduced into said host cell and thereby replicated together with the host genome. Moreover, particular vectors are capable of controlling the expression of genes to which they are functionally linked. These vectors are referred to as "expression vectors". Normally, expression vectors which may be used in DNA recombination techniques are in the form of plasmids. In the present description, "plasmid" and "vector" may be used interchangeably, since the plasmid is the most commonly used type of vector. However, the present invention is intended to comprise other types of expression vectors such as viral vectors (for example replication-deficient retroviruses, adenoviruses and adenovirus-related viruses), which exert similar functions.

The recombinant expression vectors of the invention comprise a nucleic acid of the invention in a form which is suitable for expressing said nucleic acid in a host cell, meaning that the recombinant expression vectors comprise one or more regulatory sequences which are selected on the basis of the host cells to be used for expression and which are functionally linked to the nucleic acid sequence to be expressed. In a recombinant expression vector, the term "functionally linked" means that the nucleotide sequence of interest is bound to the regulatory sequence(s) such that expression of said nucleotide sequence is possible (for example in an in vitro transcription/translation system or in a host cell, if the vector has been introduced into said host cell). The term "regulatory sequence" is intended to comprise promoters, enhancers and other expression control elements (e.g. polyadenylation signals). These regulatory sequences are described, for example, in Goeddel: Gene Expression Technology: Methods in Enzymology 185, Academic Press, San Diego, Calif. (1990). Regulatory sequences comprise those which control constitutive expression of a nucleotide sequence in many types of host cells and those which control expression of the nucleotide sequence only in particular host cells. The skilled worker understands that designing an expression vector may depend on factors such as the choice of host cell to be transformed, the desired extent of protein expression, etc. The expression vectors of the invention may be introduced into the host cells so as to prepare proteins or peptides, including fusion proteins or fusion peptides, which are encoded by the nucleic acids as described herein (e.g. SES proteins, mutated forms of SES proteins, fusion proteins, etc.).

The recombinant expression vectors of the invention may be designed for expressing SES proteins in prokaryotic or eukaryotic cells. For example, SES genes may be expressed in bacterial cells such as *C. glutamicum,* insect cells (using baculovirus expression vectors), yeast cells and other fungal cells (see Romanos, M. A. et al. (1992) "Foreign gene expression in yeast: a review", Yeast 8: 423-488; van den Hondel, C. A. M. J. J. et al. (1991) "Heterologous gene expression in filamentous fungi", in: More Gene Manipulations in Fungi, J. W. Bennet & L. L. Lasure, Editors, pp. 396-428: Academic Press: San Diego; and van den Hondel, C. A. M. J. J. & Punt, P. J. (1991) "Gene transfer systems and vector development for filamentous fungi in: Applied Molecular Genetics of Fungi, Peberdy, J. F. et al., Editors, pp. 1-28, Cambridge University Press: Cambridge), algal cells and cells of multicellular plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.: 583-586) or mammalian cells. Suitable host cells are further discussed in Goeddel, Gene Expression Technology: Methods in Enzymology 185, Academic Press, San Diego, Calif. (1990). As an alternative, the recombinant expression vector may be transcribed and translated in vitro, for example by using regulatory sequences of the T7 promoter and T7 polymerase.

Proteins are expressed in prokaryotes mainly by using vectors containing constitutive or inducible promoters which control expression of fusion or nonfusion proteins. Fusion vectors control a number of amino acids to a protein encoded therein, usually at the amino terminus of the recombinant protein. These fusion vectors usually have three tasks: 1) enhancing the expression of recombinant protein; 2) increasing the solubility of the recombinant protein; and 3) supporting the purification of the recombinant protein by acting as a ligand in affinity purification. Often a proteolytic cleavage site is introduced into fusion expression vectors at the junction of fusion unit and recombinant protein so that the recombinant protein can be separated from the fusion unit after purifying the fusion protein. These enzymes and their corresponding recognition sequences comprise factor Xa, thrombin and enterokinase.

Common fusion expression vectors comprise pGEX (Pharmacia Biotech Inc; Smith, D. B. and Johnson, K. S. (1988) Gene 67: 31-40), pMAL (New England Biolabs, Beverly, Mass.) und PRIT 5 (Pharmacia, Piscataway, N.J.), in which glutathione S-transferase (GST), maltose E-binding protein and protein A, respectively, are fused to the recombinant target protein. In one embodiment, the coding sequence of the SES protein is cloned into a pGEX expression vector such that a vector is generated, which encodes a fusion protein comprising, from N terminus to C terminus, GST—thrombin cleavage site—protein X. The fusion protein may be purified via affinity chromatography by means of a glutathione-agarose resin. The recombinant SES protein which is not fused to GST may be obtained by cleaving the fusion protein with thrombin.

Examples of suitable inducible nonfusion *E. coli* expression vectors include pTrc (Amann et al., (1988) Gene 69: 301-315) and pET 11d (Studier et al. Gene Expression Technology: Methods in Enzymology 185, Academic Press, San Diego, Calif. (1990) 60-89). The target gene expression from the pTrc vector is based on transcription from a hybrid trp-lac fusion promoter by host RNA polymerase. The target gene expression from the pET11d vector is based on transcription from a T7-gn10-lac fusion promoter, which is mediated by a coexpressed viral RNA polymerase (T7 gn1). This viral polymerase is provided by the BL 21 (DE3) or HMS174 (DE3) host strain by a resident λ prophage which harbors a T7 gn1 gene under the transcriptional control of the lacUV 5 promoter.

One strategy for maximizing expression of the recombinant protein is to express said protein in a host bacterium whose ability to proteolytically cleave said recombinant protein is disrupted (Gottesman, S. Gene Expression Technology: Methods in Enzymology 185, Academic Press, San Diego, Calif. (1990) 119-128). Another strategy is to modify the nucleic acid sequence of the nucleic acid to be inserted into an expression vector such that the individual codons for each amino acid are those which are preferably used in a bacterium selected for expression, such as *C. glutamicum* (Wada et al. (1992) Nucleic Acids Res. 20: 2111-2118). This modification of the nucleic acid sequences of the invention may be carried out by standard techniques of DNA synthesis.

In a further embodiment, the SES-protein expression vector is a yeast expression vector. Examples of vectors for expression in the yeast *S. cerevisiae* include pYepSec1 (Baldari et al., (1987) Embo J. 6: 229-234), pMFa (Kurjan and Herskowitz (1982) Cell 30: 933-943), pJRY88 (Schultz et al. (1987) Gene 54: 113-123) and pYES2 (Invitrogen Corporation, San Diego, Calif.). Vectors and methods for constructing vectors which are suitable for use in other fungi such as filamentous fungi include those which are described in detail in: van den Hondel, C. A. M. J. J. & Punt, P. J. (1991) "Gene transfer systems and vector development for filamentous fungi, in: Applied Molecular Genetics of fungi, J. F. Peberdy et al., Editors, pp. 1-28, Cambridge University Press: Cambridge.

As another alternative, it is possible to express the SES proteins of the invention in insect cells using baculovirus expression vectors. Baculovirus vectors available for expression of proteins in cultured insect cells (e.g. Sf9 cells) include the pAc series (Smith et al., (1983) Mol. Cell Biol. 3: 2156-2165) and the pVL series (Lucklow and Summers (1989) Virology 170: 31-39).

In a further embodiment, the SES proteins of the invention may be expressed in cells of unicellular plants (such as algae) or in cells of the higher plants (e.g. spermatophytes such as crops). Examples of expression vectors of plants include those which are described in detail in: Bekker, D., Kemper, E., Schell, J. and Masterson, R. (1992) "New plant binary vectors with selectable markers located proximal to the left border", Plant Mol. Biol. 20: 1195-1197; and Bevan, M. W. (1984) "Binary *Agrobacterium* vectors for plant transformation", Nucl. Acids Res. 12: 8711-8721.

A further embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6: 187-195). When used in mammalian cells, the control functions of the expression vector are often provided by viral regulatory elements. Commonly used promoters are derived, for example, from polyoma, adenovirus 2, cytomegalovirus and simian virus 40. Other suitable expression systems for prokaryotic and eukaryotic cells can be found in chapters 16 and 17 of Sambrook, J., Fritsch, E. F. and Maniatis, T., Molecular cloning: A Laboratory Manual, 2nd Edition, Cold Spring Harbor Laboratory, Cold Spring Harbor Laboratory Press, Cold Spring Harbor, N.Y., 1989.

In a further embodiment, the recombinant mammalian expression vector may preferably cause expression of the nucleic acid in a particular cell type (for example, tissue-specific regulatory elements are used for expressing the nucleic acid). Tissue-specific regulatory elements are known in the art. Non-limiting examples of suitable tissue-specific promoters include the albumin promoter (liver-specific; Pinkert et al. (1987) Genes Dev. 1: 268-277), lymphoid-specific promoters (Calame und Eaton (1988) Adv. Immunol. 43: 235-275), in particular promoters of T-cell receptors (Winoto and Baltimore (1989) EMBO J. 8: 729-733) and immunoglobulins (Banerji et al. (1983) Cell 33: 729-740; Queen and Baltimore (1983) Cell 33: 741-748), neuron-specific promoters (e.g. the neurofilament promoter; Byrne and Ruddle (1989) PNAS 86: 5473-5477), pancreas-specific promoters (Edlund et al., (1985) Science 230: 912-916) and mamma-specific promoters (e.g. milk serum promoter; U.S. Pat. No. 4,873,316 and European Patent Application document No. 264 166). Development-regulated promoters for example the murine hox promoters (Kessel and Gruss (1990) Science 249: 374-379) and the α-fetoprotein promoter (Campes and Tilghman (1989) Genes Dev. 3: 537-546), are likewise included.

Moreover, the invention provides a recombinant expression vector comprising an inventive DNA molecule which has been cloned into the expression vector in antisense direction. This means that the DNA molecule is functionally linked to a regulator sequence such that an RNA molecule which is antisense to SES mRNA can be expressed (via transcription of the DNA molecule). It is possible to select regulatory sequences which are functionally bound to a nucleic acid cloned in antisense direction and which control continuous expression of the antisense RNA molecule in a multiplicity of cell types; for example, it is possible to select viral promoters and/or enhancers or regulatory sequences which control the constitutive tissue-specific or cell type-specific expression of antisense RNA. The antisense expression vector may be in the form of a recombinant plasmid, phagemid or attenuated virus and produces antisense nucleic acids under the control of a highly effective regulatory region whose activity is determined by the cell type into which the vector is introduced. The regulation of gene expression by means of antisense genes is discussed in Weintraub, H. et al., Antisense-RNA as a molecular tool for genetic analysis, Reviews—Trends in Genetics, Vol. 1(1) 1986.

A further aspect of the invention relates to host cells into which a recombinant expression vector of the invention has been introduced. The terms "host cell" and "recombinant host cell" are used interchangeably herein. Naturally, these terms relate not only to a particular target cell but also to the progeny or potential progeny of this cell. Since particular modifications may appear in successive generations, due to mutation or environmental factors, this progeny is not necessarily identical to the parental cell but is still included within the scope of the term as used herein.

A host cell may be a prokaryotic or eukaryotic cell. For example, an SES protein may be expressed in bacterial cells such as *C. glutamicum,* insect cells, yeast cells or mammalian cells (such as Chinese hamster ovary (CHO) cells or COS cells). Other suitable host cells are familiar to the skilled worker. Microorganisms which are related to *Corynebacterium glutamicum* and can be used in a suitable manner as host cells for the nucleic acid and protein molecules of the invention are listed in Table 3.

Conventional transformation or transfection methods can be used to introduce vector DNA into prokaryotic or eukaryotic cells. The terms "transformation" and "transfection", "conjugation" and "transduction", as used herein, are intended to comprise a multiplicity of methods known in the art for introducing foreign nucleic acid (e.g. DNA) into a host cell, including calcium phosphate or calcium chloride coprecipitation, DEAE dextran-mediated transfection, lipofection, natural competence, chemically mediated transfer or electroporation. Suitable methods for transformation or transfection of host cells can be found in Sambrook et al. (Molecular Cloning: A Laboratory Manual. 2nd Edition, Cold Spring Harbor Laboratory, Cold Spring Harbor Laboratory Press, Cold Spring Harbor, N.Y., 1989) and other laboratory manuals.

In the case of stable transfection of mammalian cells, it is known that, depending on the expression vector used and transfection technique used, only a small proportion of the cells can integrate the foreign DNA into their genome. These integrants are usually identified and selected by introducing a gene which encodes a selectable marker (e.g. resistant to antibiotics) together with the gene of interest into the host cells. Preferred selectable markers include those which impart resistance to drugs such as G418, hygromycin and methotrexate. A nucleic acid which encodes a selectable marker may be introduced into a host cell on the same vector that encodes an SES protein or may be introduced in a separate vector. Cells which have been stably transfected with the introduced nucleic acid may, for example, be identified by drug selection (for example, cells which have integrated the selectable marker survive, whereas the other cells die).

A homologous recombined microorganism is generated by preparing a vector which contains at least one SES-gene section into which a deletion, addition or substitution has been introduced in order to modify, for example functionally disrupt, the SES gene. Said SES gene is preferably a *Corynebacterium glutamicum* SES gene, but it is also possible to use a homolog from a related bacterium or even from a mammalian, yeast or insect source. In a preferred embodiment, the vector is designed such that homologous recombination functionally disrupts the endogenous SES gene (i.e., the gene no longer encodes a functional protein; also referred to as "knockout" vector). As an alternative, the vector may be designed such that homologous recombination mutates or otherwise modifies the endogenous SES gene which, however, still encodes the functional protein (for example, the regulatory region located upstream may be modified such that thereby expression of the endogenous SES protein is modified.). The modified SES-gene fraction in the homologous recombination vector is flanked at its 5' and 3' ends by additional nucleic acids of the SES gene, which makes possible a homologous recombination between the exogenous SES gene carried by the vector and an endogenous SES gene in a microorganism. The length of the additional flanking SES nucleic acid is sufficient for a successful homologous recombination with the endogenous gene. Usually, the vector contains several kilobases of flanking DNA (both at the 5' and the 3' ends) (see, for example, Thomas, K. R. and Capecchi, M. R. (1987) Cell 51: 503, for a description of homologous recombination vectors). The vector is introduced into a microorganism (e.g. by electroporation) and cells in which the introduced SES gene has homologously recombined with the endogenous SES gene are selected using methods known in the art.

In another embodiment, it is possible to produce recombinant microorganisms which contain selected systems which make possible a regulated expression of the introduced gene. The insertion of an SES gene into a vector, as a result of which it is brought under the control of the lac operon, enables, for example, SES-gene expression only in the presence of IPTG. These regulatory systems are known in the art.

A host cell of the invention, such as a prokaryotic or eukaryotic host cell in culture, may be used for producing (i.e. expressing) an SES protein. Moreover, the invention provides methods for producing SES proteins by using the host cells of the invention. In one embodiment, the method comprises the cultivation of the host cell of the invention (into which a recombinant expression vector encoding an SES protein has been introduced or in whose genome a gene encoding a wild-type or modified SES protein has been introduced) in a suitable medium until the SES protein has been produced. In a further embodiment, the method comprises isolating the SES proteins from the medium or the host cell.

C. Uses and Methods of the Invention

The nucleic acid molecules, proteins, protein homologs, fusion proteins, primers, vectors and host cells described herein may be used in one or more of the following methods: identification of *C. glutamicum* and related organisms, mapping of genomes of organisms related to *C. glutamicum,* identification and localization of *C. glutamicum* sequences of interest, evolutionary studies, determination of SES-protein regions required for function, modulation of the activity of an SES protein; modulation of the metabolism of one or more cell membrane components; modulation of transmembrane transport of one or more compounds and modulation of the cellular production of a compound of interest, such as a fine chemical. The SES nucleic acid molecules of the invention have a multiplicity of uses. First, they may be used for identifying an organism as *Corynebacterium glutamicum* or close relatives thereof. They may also be used for identifying the presence of *C. glutamicum* or a relative thereof in a mixed population of microorganisms. The invention provides the nucleic acid sequences of a number of *C. glutamicum* genes. Probing the extracted genomic DNA of a culture of a uniform or mixed population of microorganisms under stringent conditions with a probe which covers a region of a *C. glutamicum* gene which is unique for this organism makes it possible to determine whether said organism is present. Although *Corynebacterium glutamicum* itself is nonpathogenic, it is related to pathogenic species such as *Corynebacterium diphtheriae.* The detection of such an organism is of substantial clinical importance.

The nucleic acid and protein molecules of the invention may futhermore serve as markers for particular regions of the genome. This is suitable not only for mapping the genome but also for functional studies of *C. glutamicum* proteins. The genomic region to which a particular *C. glutamicum* DNA-binding protein binds may be identified, for example, by cleaving the *C. glutamicum* genome and incubating the fragments with the DNA-binding protein. Those fragments which bind the protein may additionally be probed with the nucleic acid molecules of the invention, preferably by using ready detectable labels; binding of such a nucleic acid molecule to the genomic fragment makes it possible to locate the fragment on the map of the *C. glutamicum* genome, and, when carrying out the process several times using different enzymes, facilitates rapid determination of the nucleic acid sequence to which the protein binds. Moreover, the nucleic acid molecules of the invention may be sufficiently homologous to the sequences of related species for these nucleic acid molecules to serve as markers for constructing a genomic map in related bacteria (e.g. *Brevibacterium lactofermentum*).

The SES nucleic acid molecules of the invention are likewise suitable for evolutionary studies and protein structure studies. The metabolic and transport processes in which the molecules of the invention are involved are utilized by a multiplicity of prokaryotic and eukaryotic cells; comparison of the sequences of the nucleic acid molecules of the invention with those encoding similar enzymes of other organisms makes it possible to determine the degree of evolutionary relationship of said organisms. Correspondingly, such a comparison makes it possible to determine which sequence regions are conserved and which are not, and this can be helpful in determining those regions of the protein, which are essential for enzyme function. This type of determination is valuable for protein engineering studies and may give an indication as to how much mutagenesis the protein can tolerate without losing its function.

Manipulation of the SES nucleic acid molecules of the invention may cause the production of SES proteins with functional differences to wild-type SES proteins. These proteins may be improved with respect to their efficiency or activity, may be present in the cell in larger amounts than normal or may be weakened with respect to their efficiency or activity.

This modulation of the activity of proteins involved in DNA repair, recombination or transposition in *C. glutamicum* should influence the genetic stability of the cell. It is possible, for example, to reduce the ability of the cell to correct genetic errors by reducing the number or activity of proteins involved in DNA-repair mechanisms, and this should enable mutations of interest to be introduced more easily into the genome (such as those encoding proteins involved in the production of fine chemicals). The increase in the activity or number of transposons should likewise result in an increased rate of mutations in the genome and may make possible simple doubling of genes of interest (for example those encoding proteins involved in the production of fine chemicals) or disruption of undesirable genes (for example those encoding proteins for degrading fine chemicals). In contrast, reducing the number or activity of transposons or increasing the number or activity of DNA-repair proteins can possibly increase the genetic stability of *C. glutamicum,* and this in turn should result in better maintenance of introduced mutations in these microorganisms over several generations in culture. Ideally, the activity of one or more DNA repair systems is reduced and the activity of one or more transposons is increased during mutagenesis and strain construction, but the opposite happens, if the mutation of interest has been attained in the strain. This manipulation is possible by putting one or more DNA-repair genes or transposons under the control of an inducible repressor.

The modulation of proteins involved in transcription and translation in *C. glutamicum* may have direct and indirect effects on the production of a fine chemicals from these microorganisms. For example, manipulation of a protein which translates a gene directly (e.g. a polymerase) or regulates transcription directly (a repressor or activator protein) makes it possible to influence directly the expression of the target gene. In the case of genes which encode a protein involved in the biosynthesis or degradation of a fine chemical, this type of genetic manipulation should have a direct effect on the production of said fine chemical. Mutagenesis of a repressor protein so that it is no longer able to repress its target gene or mutagenesis of an activator protein so as to optimize its activity should result in increased transcription of the target gene. If the target gene is, for example, a gene of fine-chemical biosynthesis, the result may be an increased production of this chemical due to the overall larger number of for available transcripts of this gene, and this likewise should increase the amount of the protein. The increase in the amount or activity of a repressor protein for a target sequence or the reduction in the amount or activity of an activator protein for a target sequence should, if said sequence is, for example, a protein for the degradation of fine chemicals, result in a similar increase in the production of said fine chemical.

The manipulation of proteins involved in transcription and translation may also affect the production of fine chemicals indirectly. Modulation of the activity or number of transcription factors (e.g. the sigma factors) or of translational repressors/activators which regulate globally transcription in *C. glutamicum* in reaction to environmental or metabolic factors should make it possible to uncouple cellular transcription from environmental or metabolic regulation. This in turn could enable a continuous transcription under conditions which usually ought to slow down or stop gene expression, such as unfavorable conditions (e.g. high temperature, low oxygen content, high level of waste products) which are present in a large-scale fermentative culture. Increasing the rate of expression of the gene (e.g. gene of fine-chemical biosynthesis) in these situations may also increase the overall rate of the production of fine product, at least due to the comparatively larger number of proteins of fine-chemical biosynthesis in the cell. Principles and examples of modification of transcriptional and translational regulation are described, for example, in Lewin, B. (1990) Genes IV, Part 3: "Controlling procaryotic genes by transcription", Oxford Univ. Press: Oxford, pp. 213-301.

The modulation of the activity or number of proteins involved in polypeptide folding (e.g. chaperones) may make it possible overall to increase the production of correctly folded molecules in the cell. This has two effects: firstly, an overall increase in the number of proteins in the cell, due to the fact that fewer proteins are wrongly folded and degraded, and, secondly, an increase in the amount of a given protein which is correctly folded and thus active (see, for example, Thomas, J. G., Baneyx, F. (1997) Protein Expression and Purification 11(3): 289-296; Luo, Z. H., and Hua, Z. C. (1998) Biochemistry and Molecular Biology International 46(3):471-477; Dale, G. E., et al. (1994) Protein Engineering 7(7):925-931; Amrein, K. E. et al. (1995) Proc. Natl. Acad. Sci. U.S.A. 92(4):1048-1052 and Caspers, P., et al. (1994) Cell. Mol. Biol. 40(5):635-644). Although such mutations increase the number of active proteins of any kind, they may produce an additive effect on the amount of correctly folded active protein of interest, when they are coupled with additional mutations which increase the activity or amount of, for example, a protein of fine-chemical biosynthesis.

The manipulation of proteins involved in the secretion of polypeptides from *C. glutamicum,* so that their activity or number is improved, can directly improve secretion of a proteinaceous fine chemical (e.g. an enzyme) from this microorganism. It is considerably easier to harvest and purify fine chemicals if they are secreted into the medium of a large-scale culture than if they are retained in the cell, so that the yield and production of a fine chemical should increase due to this modification of the secretion system. The genetic manipulations of these secretion proteins may also lead to direct improvements of the production of one or more fine chemicals. Firstly, the increased or reduced activity of one or more *C. glutamicum* secretion systems (as it is produced by mutagenesis of one or more SES proteins involved in these pathways) may result in overall increased or reduced secretion rates from the cell. Many of these secreted proteins have functions which are important for cell viability (e.g. cell surface proteases or cell surface receptors). A change in the secretion pathway so that these proteins are transported more easily to their extracellular location may increase the overall viability of the cell and thus result in higher numbers of *C. glutamicum* cells which are able to produce fine chemicals during a large-scale cultivation. Secondly, particular bacterial secretion systems (e.g. the sec system) are known to play also a substantial part in the process by which the integral membrane proteins (e.g. channels, pores or transporters) insert into the cell membrane. If the activity of one or more secretion pathway proteins is increased, the ability of the cell to produce fine chemicals may likewise be increased, due to the presence of increased intracellular amounts of nutrients or reduced amounts of intracellular waste substances. If the activity of one or more of these secretion pathway proteins is reduced, it is possible that not enough nutrients are available for supporting the overproduction of compounds of interest or that waste products may interfere with this biosynthesis.

These abovementioned strategies for the mutagenesis of SES proteins, which ought to increase the yields of a fine chemical in *C. glutamicum,* are not intended to be limiting; variations of these mutagenesis strategies are quite obvious to the skilled worker. Using these strategies and including the mechanisms disclosed herein make it possible to use the nucleic acid and protein molecules of the invention in order to generate *C. glutamicum* or related bacterial strains expressing mutated SES nucleic acids and protein molecules so as to improve the yield, production and/or efficiency of production of a compound of interest. The compound of interest may be any product prepared by *C. glutamicum* including the end products of biosynthetic pathways and intermediates of naturally occurring metabolic pathways and also molecules which do not naturally occur in the *C. glutamicum* metabolism but are produced by a *C. glutamicum* strain of the invention.

The following examples which are not to be understood as being limiting further illustrate the present invention. The contents of all references, patent applications, patents and published patent applications cited in this patent application are hereby incorporated by way of reference.

EXAMPLES

Example 1

Preparation of Total Genomic DNA from *Corynebacterium glutamicum* ATCC13032

A *Corynebacterium glutamicum* (ATCC 13032) culture was cultivated with vigorous shaking in BHI medium (Difco) at 30° C. overnight. The cells were harvested by centrifugation, the supernatant was discarded and the cells were resuspended in 5 ml of buffer I (5% of the original culture volume—all volumes stated have been calculated for a culture volume of 100 ml). Composition of buffer I: 140.34 g/l sucrose, 2.46 g/l $MgSO_4 \cdot 7\ H_2O$, 10 ml/l $KH_2PO_4$ solution (100 g/l, adjusted to pH 6.7 with KOH), 50 ml/l M12 concentrate (10 g/l $(NH_4)_2SO_4$, 1 g/l NaCl, 2 g/l $MgSO_4 \cdot 7\ H_2O$, 0.2 g/l $CaCl_2$, 0.5 g/l yeast extract (Difco), 10 ml/l trace element mixture (200 mg/l $FeSO_4.H_2O$, 10 mg/l $ZnSO_4 \cdot 7\ H_2O$, 3 mg/l $MnCl_2 \cdot 4\ H_2O$, 30 mg/l $H_3BO_3$, 20 mg/l $CoCl_2 \cdot 6\ H_2O$, 1 mg/l $NiCl_2 \cdot 6\ H_2O$, 3 mg/l $Na_2MoO_4 \cdot 2\ H_2O$, 500 mg/l complexing agents (EDTA or citric acid), 100 ml/l vitamin mixture (0.2 ml/l biotin, 0.2 mg/l folic acid, 20 mg/l p-aminobenzoic acid, 20 mg/l riboflavin, 40 mg/l Ca panthothenate, 140 mg/l nicotinic acid, 40 mg/l pyridoxol hydrochloride, 200 mg/l myoinositol). Lysozyme was added to the suspension at a final concentration of 2.5 mg/ml. After incubation at 37° C. for approx. 4 h, the cell wall was degraded and the protoplasts obtained were harvested by centrifugation. The pellet was washed once with 5 ml of buffer I and once with 5 ml of TE buffer (10 mM Tris-HCl, 1 mM EDTA, pH 8). The pellet was resuspended in 4 ml of TE buffer and 0.5 ml of SDS solution (1.0%) and 0.5 ml of NaCl solution (5 M) were added. After addition of proteinase K at a final concentration of 200 μg/ml, the suspension was incubated at 37° C. for approx. 18 h. The DNA was purified via extraction with phenol, phenol/chloroform/isoamyl alcohol and chloroform/isoamyl alcohol by means of standard methods. The DNA was then precipitated by addition of 1/50 volume of 3 M sodium acetate and 2 volumes of ethanol, subsequent incubation at −20° C. for 30 min and centrifugation at 12 000 rpm in a high-speed centrifuge using an SS34 rotor (Sorvall) for 30 min. The DNA was dissolved in 1 ml of TE buffer containing 20 μ/g/ml RNase A and dialyzed against 1000 ml of TE buffer at 4° C. for at least 3 h. The buffer was exchanged 3 times during this period. 0.4 ml of 2 M LiCl and 0.8 ml of ethanol were added to 0.4 ml aliquots of the dialyzed DNA solution. After incubation at −20° C. for 30 min, the DNA was collected by centrifugation (13 000 rpm, Biofuge Fresco, Heraeus, Hanau, Germany). The DNA pellet was dissolved in TE buffer. It was possible to use DNA prepared by this method for all purposes, including Southern blotting and constructing genomic libraries.

Example 2

Construction of Genomic *Corynebacterium glutamicum* (ATCC13032) Banks in *Escherichia coli*

Starting from DNA prepared as described in Example 1, cosmid and plasmid banks were prepared according to known and well-established methods (see, for example, Sambrook, J. et al. (1989) "Molecular Cloning: A Laboratory Manual". Cold Spring Harbor Laboratory Press or Ausubel, F. M. et al. (1994) "Current Protocols in Molecular Biology", John Wiley & Sons).

It was possible to use any plasmid or cosmid. Particular preference was given to using the plasmids pBR322 (Sutcliffe, J. G. (1979) Proc. Natl Acad. Sci. USA, 75: 3737-3741); pACYC177 (Change & Cohen (1978) J. Bacteriol. 134: 1141-1156); pBS series plasmids (pBSSK+, pBSSK− and others; Stratagene, LaJolla, USA) or cosmids such as SuperCosl (Stratagene, LaJolla, USA) or Lorist6 (Gibson, T. J. Rosenthal, A., and Waterson, R. H. (1987) Gene 53: 283-286.

Example 3

DNA Sequencing and Functional Computer Analysis

Genomic banks, as described in Example 2, were used for DNA sequencing according to standard methods, in particular the chain termination method using ABI377 sequencers (see, for example, Fleischman, R. D. et al. (1995) "Whole-genome Random Sequencing and Assembly of *Haemophilus Influenzae* Rd., Science 269; 496-512). Sequencing primers having the following nucleotide sequences were used: 5'-GGAAACAGTATGACCATG-3' oder 5'-GTAAAACGACGGCCAGT-3'.

Example 4

In vivo Mutagenesis

In vivo mutagenesis of *Corynebacterium glutamicum* may be carried out by passing a plasmid (or other vector) DNA through *E. coli* or other microorganisms (e.g. *Bacillus* spp. or yeasts such as *Saccharomyces cerevisiae*) which cannot maintain the integrity of their genetic information. Common mutator strains contain mutations in the genes for the DNA repair system (e.g., mutHLS, mutD, mutT, etc., for comparison see Rupp, W. D. (1996) DNA repair mechanisms in *Escherichia coli* and *Salmonella,* pp. 2277-2294, ASM: Washington). These strains are known to the skilled worker. The use of these strains is illustrated, for example, in Greener, A. and Callahan, M. (1994) Strategies 7; 32-34.

Example 5

DNA Transfer between *Escherichia coli* and *Corynebacterium glutamicum*

A plurality of *Corynebacterium* and *Brevibacterium* species contain 30 endogenous plasmids (such as, for example, pHM1519 or pBL1) which replicate autonomously (for a review see, for example, Martin, J. F. et al. (1987) Biotechnology 5: 137-146). Shuttle vectors for *Escherichia coli* and *Corynebacterium glutamicum* can be constructed readily by means of standard vectors for *E. coli* (Sambrook, J. et al., (1989), "Molecular Cloning: A Laboratory Manual", Cold Spring Harbor Laboratory Press or Ausubel, F. M. et al. (1994) "Current Protocols in Molecular Biology", John Wiley & Sons), to which an origin of replication for and a suitable marker from *Corynebacterium glutamicum* is added. Such origins of replication are preferably taken from endogenous plasmids which have been isolated from *Corynebacterium* and *Brevibacterium* species. Particular use as transformation markers for these species are genes for kanamycin resistance (such as those derived from the Tn5 or the Tn903 transposon) or for chloramphenicol (Winnacker, E. L. (1987) "From Genes to Clones—Introduction to Gene Technology, VCH, Weinheim). There are numerous examples in the literature for preparing a large multiplicity of shuttle vectors which replicate in *E. coli* and *C. glutamicum* and which can be used for various purposes, including the overexpression of genes (see, for example, Yoshihama, M. et al. (1985) J. Bacteriol. 162: 591-597, Martin, J. F. et al., (1987) Biotechnology, 5: 137-146 and Eikmanns, B. J. et al. (1992) Gene 102: 93-98).

Standard methods make it possible to clone a gene of interest into one of the above-described shuttle vectors and to introduce such hybrid vectors into *Corynebacterium glutamicum* strains. *C. glutamicum* can be transformed via protoplast transformation (Kastsumata, R. et al., (1984) J. Bacteriol. 159, 306-311), electroporation (Liebl, E. et al., (1989) FEMS Microbiol. Letters, 53: 399-303) and, in cases in which specific vectors are used, also via conjugation (as described, for example, in Schäfer, A., et al. (1990) J. Bacteriol. 172: 1663-1666). Likewise, it is possible to transfer the shuttle vectors for *C. glutamicum* to *E. coli* by preparing plasmid DNA from *C. glutamicum* (by means of standard methods known in the art) and transforming it into *E. coli.* This transformation step can be carried out using standard methods but advantageously an Mcr-deficient *E. coli* strain such as NM522 (Gough & Murray (1983) J. Mol. Biol. 166: 1-19) is used.

Example 6

Determination of the Expression of the Mutant Protein

The observations of the activity of a mutated protein in a transformed host cell are based on the fact that the mutant protein is expressed in a similar manner and in similar quantity to the wild-type protein. A suitable method for determining the amount of transcription of the mutant gene (an indication of the amount of mRNA available for translation of the gene product) is to carry out a Northern blot (see, for example, Ausubel et al., (1988) Current Protocols in Molecular Biology, Wiley: New York), with a primer which is designed such that it binds to the gene of interest being provided with a detectable (usually radioactive or chemiluminescent) label such that—when the total RNA of a culture of the organism is extracted, fractionated on a gel, transferred to a stable matrix and incubated with this probe—binding and binding quantity of the probe indicate the presence and also the amount of mRNA for said gene. This information is an indication of the extent to which the mutant gene has been transcribed. Total cell RNA can be isolated from *Corynebacterium glutamicum* by various methods known in the art, as described in Bormann, E. R. et al., (1992) Mol. Microbiol. 6: 317-326.

The presence or the relative amount of protein translated from said mRNA can be determined by using standard techniques such as Western blot (see, for example, Ausubel et al. (1988) "Current. Protocols in Molecular Biology", Wiley, New York). In this method, total cell proteins are extracted, fractionated by gel electrophoresis, transferred to a matrix such as nitrocellulose and incubated with a probe, for example an antibody, which binds specifically to the protein of interest. This probe is usually provided with a chemiluminescent or colorimetric label which can be readily detected. The presence and the observed amount of label indicate the presence and the amount of the desired mutant protein in the cell.

Example 7

Growth of Genetically Modified *Corynebacterium glutamicum*—Media and Cultivation Conditions Genetically modified corynebacteria are cultivated in synthetic or natural growth media. A number of different growth media for corynebacteria are known and readily available (Lieb et al. (1989) Appl. Microbiol. Biotechnol. 32: 205-210; von der Osten et al. (1998) Biotechnology Letters 11: 11-16; Patent DE 4 120 867; Liebl (1992) "The Genus *Corynebacterium*", in: The Procaryotes, Vol. II, Balows, A., et al., editors Springer-Verlag). These media are composed of one or more carbon sources, nitrogen sources, inorganic salts, vitamins and trace elements. Preferred carbon sources are sugars such as mono-, di- or polysaccharides. Examples of very good carbon sources are glucose, fructose, mannose, galactose, ribose, sorbose, ribulose, lactose, maltose, sucrose, raffinose, starch and cellulose. Sugars may also be added to the media via complex compounds such as molasses or other byproducts from sugar refining. It may also be advantageous to add mixtures of various carbon sources. Other possible carbon sources are alcohols and organic acids, such as methanol, ethanol, acetic acid or lactic acid. Nitrogen sources are usually organic or inorganic nitrogen compounds or materials containing these compounds. Examples of nitrogen sources include ammonia gas and ammonium salts such as $NH_4Cl$ or $(NH_4)_2SO_4$, $NH_4OH$, nitrates, urea, amino acids and complex nitrogen sources such as cornsteep liquor, soya meal, soya protein, yeast extracts, meat extract and others.

Inorganic salt compounds which may be present in the media include the chloride, phosphorus or sulfate salts of calcium, magnesium, sodium, cobalt, molybdenum, potassium, manganese, zinc, copper and iron. Chelating agents may be added to the medium in order to keep the metal ions in solution. Particularly suitable chelating agents include dihydroxyphenols such as catechol or protocatechuate and organic acids such as citric acid. The media usually also contain other growth factors such as vitamins or growth promoters, examples of which include biotin, riboflavin, thiamine, folic acid, nicotinic acid, panthothenate and pyridoxine. Growth factors and salts are frequently derived from complex media components such as yeast extract, molasses, cornsteep liquor and the like. The exact composition of the media heavily depends on the particular experiment and is decided upon individually for each specific case. Information on the optimization of media can be found in the textbook "Applied Microbiol. Physiology, A Practical Approach" (editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) or others.

All media components are sterilized, either by heat (20 min at 1.5 bar and 121° C.) or by sterile filtration. The components may be sterilized either together or, if required, separately. All media components may be present at the start of the cultivation or added continuously or batchwise, as desired.

The cultivation conditions are defined separately for each experiment. The temperature should be between 15° C. and 45° C. and may be kept constant or may be altered during the experiment. The pH of the medium should be in the range from 5 to 8.5, preferably around 7.0 and may be maintained by adding buffers to the media. An example of a buffer for this purpose is a potassium phosphate buffer. Synthetic buffers such as MOPS, HEPES; ACES, etc. may be used alternatively or simultaneously. Addition of NaOH or $NH_4OH$ can also keep the pH constant during cultivation. If complex media components such as yeast extract are used, the demand for additional buffers decreases, since many complex compounds have a high buffer capacity. In the case of using a fermenter for cultivating microorganisms, the pH may also be regulated using gaseous ammonia.

The incubation period is usually in a range from several hours to several days. This time is selected such that the maximum amount of product accumulates in the broth. The growth experiments disclosed may be carried out in a multiplicity of containers such as microtiter plates, glass tubes, glass flasks or glass or metal fermenters of different sizes. For the screening of a large number of clones, the microorganisms should be grown in microtiter plates, glass tubes or shaker flasks either with or without baffles. Preference is given to using 100 ml shaker flasks which are filled with 10% (based on volume) of the required growth medium. The flasks should be shaken on an orbital shaker (amplitude 25 mm) at a speed in the range of 100-300 rpm. Losses due to evaporation can be reduced by maintaining a humid atmosphere; alternatively, the losses due to evaporation should be corrected mathematically.

If genetically modified clones are investigated, an unmodified control clone or a control clone containing the basic plasmid without insert should also be assayed. The medium is inoculated to an $OD_{600}$ of 0.5-1.5, with cells being used which have been grown on agar plates such as CM plates (10 g/l glucose, 2.5 g/l NaCl, 2 g/l urea, 10 g/l polypeptone, 5 g/l yeast extract, 5 g/l meat extract, 22 g/l agar pH 6.8 with 2 M NaOH) which have been incubated at 30° C. The media are inoculated either by introducing a saline solution of *C. glutamicum* cells from CM plates or by adding a liquid preculture of said bacterium.

Example 8

In vitro Analysis of the Function of Mutant Proteins

The determination of the activities and kinetic parameters of enzymes is well known in the art. Experiments for determining the activity of a particular modified enzyme must be adapted to the specific activity of the wild-type enzyme, and this is within the capabilities of the skilled worker. Overviews regarding enzymes in general and also specific details concerning the structure, kinetics, principles, methods, applications and examples of the determination of many enzyme activities can be found, for example, in the following references: Dixon, M., and Webb, E. C: (1979) Enzymes, Longmans, London; Fersht (1985) Enzyme Structure and Mechanism, Freeman, New York; Walsh (1979) Enzymatic Reaction Mechanisms. Freeman, San Francisco; Price, N. C., Stevens, L. (1982) Fundamentals of Enzymology. Oxford Univ. Press: Oxford; Boyer, P. D: editors (1983) The Enzymes, 3rd edition, Academic Press, New York; Bisswanger, H. (1994) Enzymkinetik, 2nd edition VCH, Weinheim (ISBN 3527300325); Bergmeyer, H. U., Bergmeyer, J., Graβl, M. editors (1983-1986) Methods of Enzymatic Analysis, 3rd edition, Vol. I-XII, Verlag Chemie: Weinheim; and Ullmann's Encyclopedia of Industrial Chemistry (1987) Vol. A9, "Enzymes", VCH, Weinheim, pp. 352-363.

The activity of proteins binding to DNA can be measured by many well-established methods such as DNA bandshift assays (which are also referred to as gel retardation assays). The action of these proteins on the expression of other molecules can be measured using reporter gene assays (as described in Kolmar, H. et al., (1995) EMBO J. 14: 3895-3904 and in references therein). Reporter gene assay systems are well known and established for applications in prokaryotic and eukaryotic cells, with enzymes such as beta-galactosidase, green fluorescent protein and several other enzymes being used.

The activity of membrane transport proteins can be determined according to techniques described in Gennis, R. B. (1989) "Pores, Channels and Transporters", in Biomembranes, Molecular Structure and Function, Springer: Heidelberg, pp. 85-137; 199-234; and 270-322.

Example 9

Analysis of the Influence of Mutated Protein on the Production of the Product of Interest The effect of the genetic modification in *C. glutamicum* on the production of a compound of interest (such as an amino acid) can be determined by growing the modified microorganisms under suitable conditions (such as those described above) and testing the medium and/or the cellular components with regard to increased production of the product of interest (i.e. an amino acid). Such analytical techniques are well known to the skilled worker and include spectroscopy, thin-layer chromatography, various types of coloring methods, enzymic and microbiological methods and analytical chromatography such as high performance liquid chromatography (see, for example, Ullman, Encyclopedia of Industrial Chemistry, Vol. A2, pp. 89-90 and pp. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", pp. 469-714, VCH: Weinheim; Belter, P. A. et al. (1988) Bioseparations: downstream processing for Biotechnology, John Wiley and Sons; Kennedy, J. F. and Cabral, J. M. S. (1992) Recovery processes for biological Materials, John Wiley and Sons; Shaeiwitz, J. A. and Henry, J. D. (1988) Biochemical Separations, in Ullmann's Encyclopedia of Industrial Chemistry, Vol. B3; Chapter 11, pp. 1-27, VCH: Weinheim; and Dechow, F. J. (1989) Separation and purification techniques in biotechnology, Noyes Publications).

In addition to measuring the end product of the fermentation, it is likewise possible to analyze other components of the metabolic pathways, which are used for producing the compound of interest, such as intermediates and byproducts, in order to determine the overall efficiency of production of the compound. The analytical methods include measuring the amounts of nutrients in the medium (for example sugars, hydrocarbons, nitrogen sources, phosphate and other ions), measuring biomass composition and growth, analyzing the production of common metabolites from biosynthetic pathways and measuring gases generated during fermentation. Standard methods for these measurements are described in Applied Microbial Physiology; A Practical Approach, P. M. Rhodes and P. F. Stanbury, editors IRL Press, pp. 103-129; 131-163 and 165-192 (ISBN: 0199635773) and the references therein.

Example 10

Purification of the Product of Interest from a *C. glutamicum* Culture

The product of interest may be obtained from *C. glutamicum* cells or from the supernatant of the above-described culture by various methods known in the art. If the product of interest is not secreted by the cells, the cells may be harvested from the culture by slow centrifugation, and the cells may be lysed by standard techniques such as mechanial force or sonication. The cell debris is removed by centrifugation and the supernatant fraction which contains the soluble proteins is obtained for further purification of the compound of interest. If the product is secreted by the *C. glutamicum* cells, the cells are removed from the culture by slow centrifugation and the supernatant fraction is retained for further purification.

The supernatant fraction from both purification methods is subjected to chromatography using a suitable resin, and either the molecule of interest is retained on the chromatography resin while many contaminants in the sample are not, or the contaminants remain on the resin while the sample does not. If necessary, these chromatography steps can be repeated using the same or different chromatography resins. The skilled worker is familiar with the selection of suitable chromatography resins and the most effective application for a particular molecule to be purified. The purified product may be concentrated by filtration or ultrafiltration and stored at a temperature at which product stability is highest.

In the art, many purification methods are known and the above purification method is not intended to be limiting. These purification techniques are described, for example, in Bailey, J. E. & Ollis, D. F. Biochemical Engineering Fundamentals, McGraw-Hill: New York (1986).

The identity and purity of the isolated compounds can be determined by techniques of the prior art. These techniques comprise high performance liquid chromatography (HPLC), spectroscopic methods, coloring methods, thin-layer chromatography, NIRS, enzyme assays or microbiological assays. These analytical methods are compiled in: Patek et al. (1994) Appl. Environ. Microbiol. 60: 133-140; Malakhova et al. (1996) Biotekhnologiya 11: 27-32; and Schmidt et al. (1998) Bioprocess Engineer. 19: 67-70. Ullmann's Encyclopedia of Industrial Chemistry (1996) Vol. A27, VCH: Weinheim, pp. 89-90, pp. 521-540, pp. 540-547, pp.

559-566, 575-581 and pp. 581-587; Michal, G (1999) Biochemical Pathways:. An Atlas of Biochemistry and Molecular Biology, John Wiley and Sons; Fallon, A. et al. (1987) Applications of HPLC in Biochemistry in: Laboratory Techniques in Biochemistry and Molecular Biology, Vol. 17.

Equivalents

The skilled worker knows, or can identify by using simply routine methods, a large number of equivalents of the specific embodiments of the invention. These equivalents are intended to be included in the patent claims below.

The information in Table 1 is to be understood as follows:

In column 1, "DNA ID", the relevant number refers in each case to the SEQ ID NO of the enclosed sequence listing. Consequently, "5" in column "DNA ID" is a reference to SEQ ID NO:5.

In column 2, "AA ID", the relevant number refers in each case to the SEQ ID NO of the enclosed sequence listing. Consequently, "6" in column "AA ID" is a reference to SEQ ID NO:6.

In column 3, "Identification", an unambiguous internal name for each sequence is listed.

In column 4, "AA pos", the relevant number refers in each case to the amino acid position of the polypeptide sequence "AA ID" in the same row. Consequently, "26" in column "AA pos" is amino acid position 26 of the polypeptide sequence indicated accordingly. Position counting starts at the N terminus with +1.

In column 5, "AA wild type", the relevant letter refers in each case to the amino acid, displayed in the one-letter code, at the position in the corresponding wild-type strain, which is indicated in column 4.

In column 6, "AA mutant", the relevant letter refers in each case to the amino acid, displayed in the one-letter code, at the position in the corresponding mutant strain, which is indicated in column 4.

In column 7, "Function", the physiological function of the corresponding polypeptide sequence is listed.

One-letter code of the proteinogenic amino acids:

A Alanine

C Cysteine

D Aspartic acid,

E Glutamic acid

F Phenylalanine

G Glycine

H His

I Isoleucine

K Lysine

L Leucine

M Methionine

N Asparagine

P Proline

Q Glutamine

R Arginine

S Serine

T Threonine

V Valine

W Tryptophan

Y Tyrosine

TABLE 1

Genes coding for proteins for genetic stability, gene expression and folding

| DNA ID: | AA ID: | Identification: | AA pos: | AA wild type | AA mutant | Function: |
|---|---|---|---|---|---|---|
| 1 | 2 | RXA00019 | 337 | P | S | SINGLE-STRANDED-DNA-SPECIFIC EXONUCLEASE RECJ (EC 3.1.—.—) |
| | | | 405 | T | I | SINGLE-STRANDED-DNA-SPECIFIC EXONUCLEASE RECJ (EC 3.1.—.—) |
| | | | 504 | P | S | SINGLE-STRANDED-DNA-SPECIFIC EXONUCLEASE RECJ (EC 3.1.—.—) |
| 3 | 4 | RXA00061 | 754 | S | N | DNA POLYMERASE I (EC 2.7.7.7) |
| 5 | 6 | RXA00209 | 414 | V | A | GLUTAMYL-TRNA(GLN) AMIDOTRANSFERASE SUBUNIT A (EC 6.3.5.—) |
| | | | 454 | L | F | GLUTAMYL-TRNA(GLN) AMIDOTRANSFERASE SUBUNIT A (EC 6.3.5.—) |
| 7 | 8 | RXA00211 | 44 | V | I | GLUTAMYL-TRNA(GLN) AMIDOTRANSFERASE SUBUNIT B (EC 6.3.5.—) |
| 9 | 10 | RXA00314 | 319 | E | K | CYSTEINYL-TRNA SYNTHETASE (EC 6.1.1.16) |
| 11 | 12 | RXA00458 | 170 | L | F | GLUTAMYL-TRNA SYNTHETASE (EC 6.1.1.17) |
| 13 | 14 | RXA00493 | 363 | A | T | 60 KD CHAPERONIN GROEL |
| 15 | 16 | RXA00588 | 23 | A | V | TRANSCRIPTION ELONGATION FACTOR GREA |
| 17 | 18 | RXA00669 | 68 | A | T | TRNA PSEUDOURIDINE SYNTHASE A (EC 4.2.1.70) |
| 19 | 20 | RXA01061 | 686 | P | S | LEUCYL-TRNA SYNTHETASE (EC 6.1.1.4) |
| 21 | 22 | RXA01277 | 704 | G | S | PROLYL ENDOPEPTIDASE (EC 3.4.21.26) |
| 23 | 24 | RXA01278 | 543 | T | I | Protein Translation Elongation Factor G (EF-G) |
| 25 | 26 | RXA01284 | 164 | D | N | Bacterial Protein Translation Elongation Factor Tu (EF-TU) |
| | | | 362 | S | F | Bacterial Protein Translation Elongation Factor Tu (EF-TU) |
| 27 | 28 | RXA01344 | 5 | P | L | DNA-DIRECTED RNA POLYMERASE BETA CHAIN (EC 2.7.7.6) |
| | | | 429 | D | V | DNA-DIRECTED RNA POLYMERASE BETA CHAIN (EC 2.7.7.6) |
| 29 | 30 | RXA01345 | 308 | A | V | DNAK PROTEIN |
| 31 | 32 | RXA01404 | 108 | T | I | TRANSCRIPTIONAL REPRESSOR |
| 33 | 34 | RXA01431 | 46 | A | T | THIOREDOXIN |
| 35 | 36 | RXA01438 | 182 | A | T | FERREDOXIN—NADP REDUCTASE (EC 1.18.1.2) |
| 37 | 38 | RXA01490 | 277 | A | V | TRNA PSEUDOURIDINE SYNTHASE B (EC 4.2.1.70) |
| 39 | 40 | RXA01493 | 32 | A | V | Na+ DRIVEN MULTIDRUG EFFLUX PUMP |
| 41 | 42 | RXA01559 | 400 | T | A | PROTEIN TRANSLOCASE SUBUNIT SECD |
| 43 | 44 | RXA01596 | 334 | R | C | DNA REPAIR PROTEIN RECN |
| | | | 493 | G | D | DNA REPAIR PROTEIN RECN |
| 45 | 46 | RXA01651 | 7 | S | F | TRANSPOSASE |
| | | | 33 | L | F | TRANSPOSASE |
| 47 | 48 | RXA01710 | 69 | P | S | TRANSCRIPTIONAL REGULATOR |
| 49 | 50 | RXA01852 | 120 | P | S | HISTIDYL-TRNA SYNTHETASE (EC 6.1.1.21) |

TABLE 1-continued

Genes coding for proteins for genetic stability, gene expression and folding

| DNA ID: | AA ID: | Identification: | AA pos: | AA wild type | AA mutant | Function: |
|---|---|---|---|---|---|---|
| 51 | 52 | RXA01913 | 61 | L | F | Protein Translation Elongation Factor Ts (EF-Ts) |
| 53 | 54 | RXA02145 | 321 | P | L | MENAQUINOL-CYTOCHROME C REDUCTASE CYTOCHROME B SUBUNIT |
| 55 | 56 | RXA02236 | 87 | L | F | Integration host factor |
| 57 | 58 | RXA02267 | 65 | A | T | DNA (CYTOSINE-5)-METHYLTRANSFERASE (EC 2.1.1.37) |
| 59 | 60 | RXA02280 | 502 | A | V | HEAT SHOCK PROTEIN HTPG |
| 61 | 62 | RXA02388 | 401 | E | K | COME OPERON PROTEIN 3 |
| | | | 451 | V | M | COME OPERON PROTEIN 3 |
| 63 | 64 | RXA02416 | 484 | G | D | EXCINUCLEASE ABC SUBUNIT A |
| 65 | 66 | RXA02418 | 45 | V | I | Bacterial Protein Translation Initiation Factor 3 (IF-3) |
| 67 | 68 | RXA02429 | 670 | M | I | PROTEIN TRANSLOCASE SUBUNIT SECA |
| 69 | 70 | RXA02431 | 73 | A | V | DNA POLYMERASE IV |
| 71 | 72 | RXA02445 | 17 | G | E | ATP-DEPENDENT DNA HELICASE RECG |
| 73 | 74 | RXA02476 | 167 | S | F | A/G-SPECIFIC ADENINE GLYCOSYLASE (EC 3.2.2.—) |
| 75 | 76 | RXA02726 | 286 | A | V | ISOLEUCYL-TRNA SYNTHETASE (EC 6.1.1.5) |
| 77 | 78 | RXA02731 | 374 | E | K | EXCINUCLEASE ABC SUBUNIT B |
| | | | 398 | M | L | EXCINUCLEASE ABC SUBUNIT B |
| | | | 410 | R | L | EXCINUCLEASE ABC SUBUNIT B |
| 79 | 80 | RXA02736 | 312 | S | F | PUTATIVE OXPPCYCLE PROTEIN OPCA |
| 81 | 82 | RXA02742 | 179 | G | S | DNA/RNA HELICASE (DEAD/DEAH BOX FAMILY) |
| 83 | 84 | RXA02748 | 100 | P | S | SIGNAL RECOGNITION PARTICLE, SUBUNIT FFH/SRP54 |
| | | | 164 | G | D | SIGNAL RECOGNITION PARTICLE, SUBUNIT FFH/SRP54 |
| 85 | 86 | RXA03070 | 249 | A | V | TRANSPOSASE |
| 87 | 88 | RXA03098 | 164 | S | N | DNA alkylation repair enzyme |
| 89 | 90 | RXA03206 | 98 | G | D | D-Tyr-tRNATyr deacylase |
| 91 | 92 | RXA03260 | 56 | S | F | TRANSPOSASE |
| 93 | 94 | RXA03394 | 11 | S | F | METHIONYL-TRNA SYNTHETASE (EC 6.1.1.10) |
| 95 | 96 | RXA03674 | 342 | V | I | ATP-DEPENDENT HELICASE HEPA |
| 97 | 98 | RXA03793 | 414 | A | V | RNA POLYMERASE SIGMA FACTOR RPOD |
| 99 | 100 | RXA06048 | 3 | L | F | PS1 PROTEIN PRECURSOR |
| | | | 4 | L | P | PS1 PROTEIN PRECURSOR |
| | | | 5 | T | S | PS1 PROTEIN PRECURSOR |
| | | | 9 | A | T | PS1 PROTEIN PRECURSOR |
| | | | 26 | I | V | PS1 PROTEIN PRECURSOR |
| | | | 31 | S | T | PS1 PROTEIN PRECURSOR |
| | | | 66 | S | N | PS1 PROTEIN PRECURSOR |
| | | | 158 | N | D | PS1 PROTEIN PRECURSOR |
| 101 | 102 | RXA07005 | 339 | P | S | PROBABLE ATP-DEPENDENT HELICASE LHR (EC 3.6.1.—) |
| 103 | 104 | RXA07006 | 239 | P | L | EXODEOXYRIBONUCLEASE VII LARGE SUBUNIT (EC 3.1.11.6) |

We claim:

1. An isolated nucleic acid molecule encoding the amino acid sequence set forth in SEQ ID NO:30, wherein the amino acid residue at position 308 of SEQ ID NO:30 is any amino acid except alanine, or a complement thereof.

2. The isolated nucleic acid molecule of claim 1 wherein the amino acid residue at position 308 of SEQ ID NO:30 is valine.

3. An isolated nucleic acid molecule which hybridizes to the complement of the nucleotide sequence set forth in SEQ ID NO:29 at 6X sodium chloride/sodium citrate (SSC) at 45° C. followed by one or more washes in 0.2 X SSC, 0.1% SDS at 50-65° C., wherein the nucleic acid molecule encodes any amino acid except alanine at the position corresponding to nucleotide residues 1022-1024 of SEQ ID NO:29, and wherein the nucleic acid molecule encodes a polypeptide which has a DNAK protein activity, or a complement thereof.

4. An isolated nucleic acid molecule comprising the nucleotide sequence set forth in SEQ ID NO:29, wherein the nucleic acid molecule comprises one or more nucleic acid modifications at nucleotide residues 1022-1024 of SEQ ID NO:29 such that nucleotide residues 1022-1024 of SEQ ID NO:29 encode any amino acid except alanine, or a complement thereof.

5. A vector comprising the nucleic acid molecule of any one of claims 1, 3 or 4.

6. The vector of claim 5, which is an expression vector.

7. An isolated host cell, which is transfected with the vector of claim 6.

8. The host cell of claim 7, wherein expression of said nucleic acid molecule modulates the production of a fine chemical from said cell.

9. A method for preparing a fine chemical, comprising culturing the cell of claim 7 such that the fine chemical is produced.

10. The method of claim 9, wherein the fine chemical is an amino acid.

11. The method of claim 10, wherein said amino acid is lysine.

12. The host cell of claim 7, wherein said cell is a microorganism.

13. The host cell of claim 12, wherein said cell belongs to the genus *Corynebacrerium* or *Brevibacterium*.

14. The host cell of claim 8, wherein said fine chemical is selected from the group consisting of organic acids, proteinogenic and nonproteinogenic amino acids, purine and pyrimidine bases, nucleosides, nucleotides, lipids, saturated and unsaturated fatty acids, diols, carbohydrates, aromatic compounds, vitamins, cofactors and enzymes.

15. The method of claim 9, wherein said cell belongs to the genus *Corynebacrerium* or *Brevibacterium*.

16. The method of claim 9, wherein expression of the nucleic acid molecule from said vector results in modulation of production of said fine chemical.

17. A method for producing a fine chemical, comprising culturing a cell whose genomic DNA has been altered by the inclusion of a nucleic acid molecule of any one of claims 1, 3 or 4.

18. The nucleic acid molecule of claim 4, wherein nucleotide residues 1022-1024 of SEQ ID NO:29 encode valine.

19. The nucleic acid molecule of claim 3, wherein the nucleic acid molecule encodes valine at the position corresponding to nucleotide residues 1022-1024 of SEQ ID NO:29.

* * * * *